(12) United States Patent
Basit et al.

(10) Patent No.: US 11,464,745 B2
(45) Date of Patent: Oct. 11, 2022

(54) SOLID PHARMACEUTICAL DOSAGE FORMULATIONS AND PROCESSES

(71) Applicant: UCL Business PLC, London (GB)

(72) Inventors: Abdul Basit, London (GB); Alvaro Goyanes, London (GB); Simon Gaisford, London (GB); Fabrizio Fina, London (GB)

(73) Assignee: UCL Business PLC, London (GB)

( * ) Notice: Subject to any disclaimer, the term of this patent is extended or adjusted under 35 U.S.C. 154(b) by 158 days.

(21) Appl. No.: 16/463,728

(22) PCT Filed: Nov. 27, 2017

(86) PCT No.: PCT/GB2017/053558
§ 371 (c)(1),
(2) Date: May 23, 2019

(87) PCT Pub. No.: WO2018/096363
PCT Pub. Date: May 31, 2018

(65) Prior Publication Data
US 2019/0374471 A1     Dec. 12, 2019

(30) Foreign Application Priority Data
Nov. 28, 2016 (GB) .................................. 1620066

(51) Int. Cl.
| | |
|---|---|
| *A61K 9/20* | (2006.01) |
| *A61K 9/00* | (2006.01) |
| *A61K 9/16* | (2006.01) |
| *A61K 9/70* | (2006.01) |
| *A61K 31/167* | (2006.01) |
| *A61K 31/606* | (2006.01) |
| *B33Y 10/00* | (2015.01) |
| *B33Y 30/00* | (2015.01) |
| *B33Y 70/00* | (2020.01) |
| *B33Y 80/00* | (2015.01) |

(52) U.S. Cl.
CPC ............ *A61K 9/2095* (2013.01); *A61K 9/006* (2013.01); *A61K 9/0056* (2013.01); *A61K 9/1617* (2013.01); *A61K 9/1635* (2013.01); *A61K 9/2009* (2013.01); *A61K 9/2018* (2013.01); *A61K 9/2031* (2013.01); *A61K 9/2054* (2013.01); *A61K 9/703* (2013.01); *A61K 31/167* (2013.01); *A61K 31/606* (2013.01); *B33Y 10/00* (2014.12); *B33Y 30/00* (2014.12); *B33Y 70/00* (2014.12); *B33Y 80/00* (2014.12)

(58) Field of Classification Search
CPC .......... A61K 9/16; A61K 9/1682; A61K 9/20; A61K 9/2004; A61K 9/50; A61K 9/5089; A61K 9/205; A61K 9/2054
See application file for complete search history.

(56) References Cited

U.S. PATENT DOCUMENTS

| | | | |
|---|---|---|---|
| 2003/0186162 A1* | 10/2003 | Takahashi | ................ B41N 1/14 430/270.1 |
| 2018/0110250 A1* | 4/2018 | Popplewell | ............ A61K 8/922 |

FOREIGN PATENT DOCUMENTS

| | | | | |
|---|---|---|---|---|
| CN | 103656752 A | 3/2014 | | |
| WO | 95/11007 A1 | 4/1995 | | |
| WO | 01/87272 A2 | 11/2001 | | |
| WO | 2015/143553 A1 | 10/2015 | | |
| WO | WO-2015143553 A1 * | 10/2015 | ......... | A61C 13/0018 |
| WO | 2016/139240 A1 | 9/2016 | | |
| WO | 2017/165624 A1 | 9/2017 | | |

OTHER PUBLICATIONS

Wang et al (Stereolithographic (SLA) 3D printing of oral modified-release dosage forms; International Journal of Pharmaceutics 503, 2016, 207-212) (Year: 2016).*
Leong et al. (Fabrication of porous polymeric matrix drug delivery devices using the selective laser sintering technique; Proc Instn Meeh Engrs vol. 2015, Part H) (Year: 2015).*
J. Betka etal (Lasers in otorhinolaryngology (ORL); Lasers for Medical Applications, 2013) (Year: 2013).*
International Search Report and Written Opinion of PCT/GB2017/053558 dated Jan. 26, 2018, 16 pages.
E. Antonov et al., Adv Mater. Dec. 20, 2004; 17(3): 327-330.
K. Leong et al., Bio-Medical Materials and Engineering 17 (2007) 147-157.
G. Salmoria et al., Int J. Adv Manuf Technol (2013) 66:1113-1118.
Translation of CN 103656752A.
Mohamed A. Alhnan et al., "Emergence of 3D Printed Dosage Forms: Opportunities and Challenges", Pharm Res., published online: May 18, 2016.

\* cited by examiner

*Primary Examiner* — Micah Paul Young
(74) *Attorney, Agent, or Firm* — Quarles & Brady LLP

(57) ABSTRACT

A process for producing a solid pharmaceutical dosage formulation, said process comprising powder bed fusion selective laser 3-dimensional printing of a mixture comprising: (a)a drug; and (b)an excipient; whereinat least one of said drug and said excipient absorbs electromagnetic radiation at a wavelength emitted by the laser; or (a)a drug; (b)an excipient; and (c)an absorbent material which absorbs electromagnetic radiation at a wavelength emitted by the laser.

20 Claims, 11 Drawing Sheets

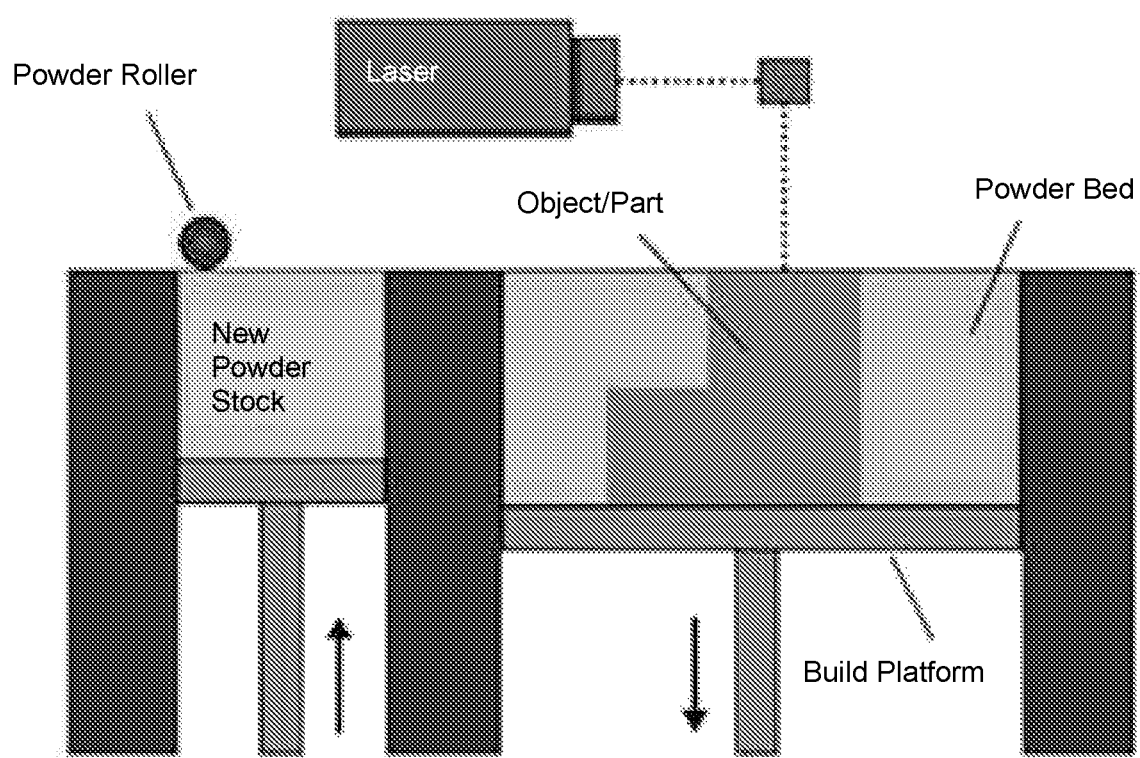
Figure 1 – Powder Bed Fusion Selective Laser 3DP Methods

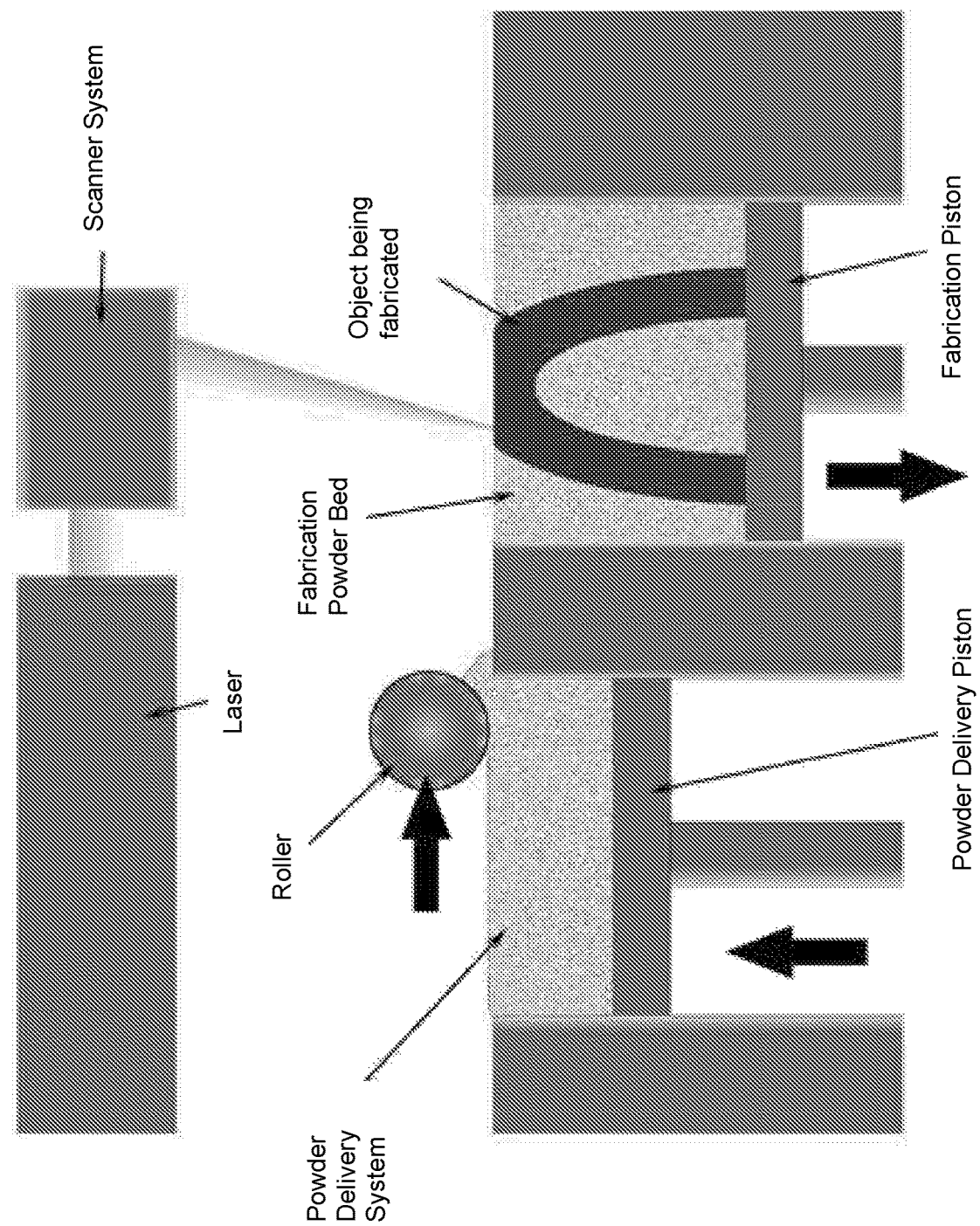
Figure 2 – Selective Laser Sintering 3DP (part 1)

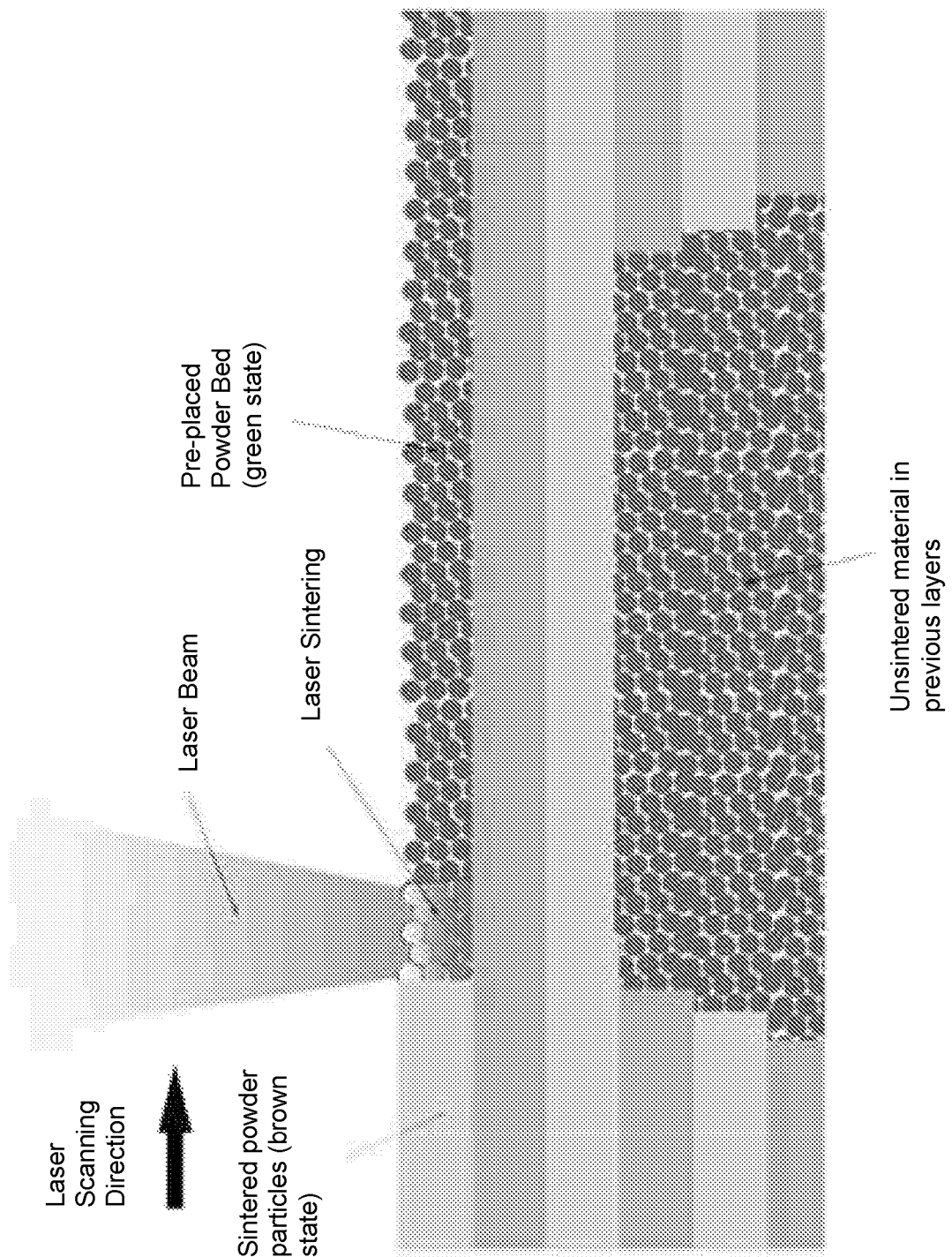
Figure 2 continued – Selective Laser Sintering 3DP (part 2)

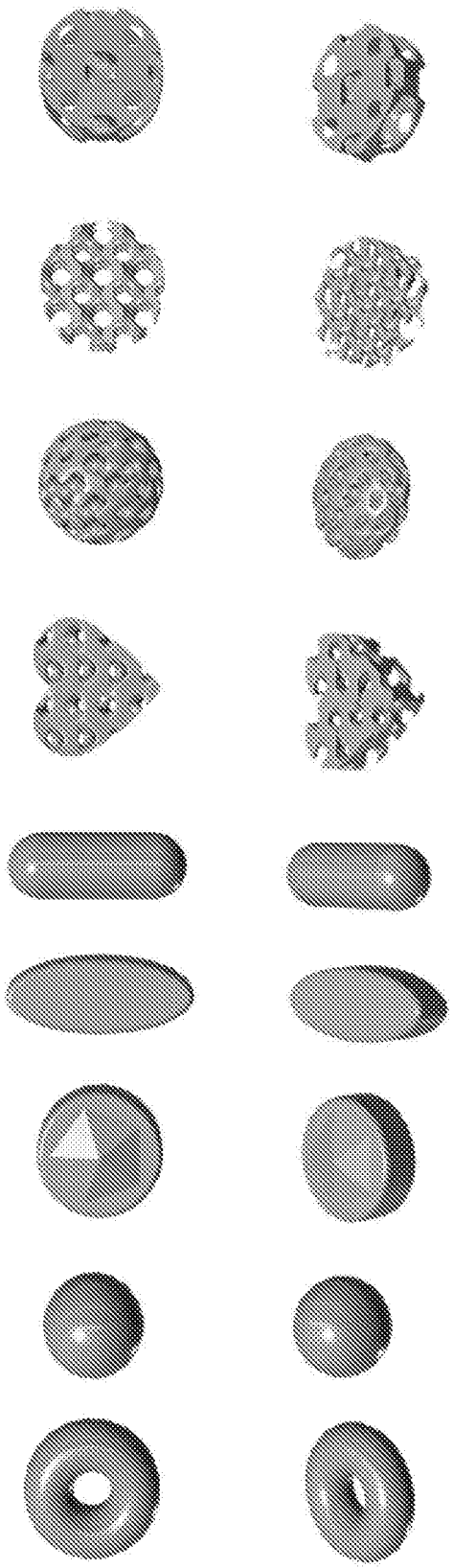
Figure 3 – typical 3DP geometries
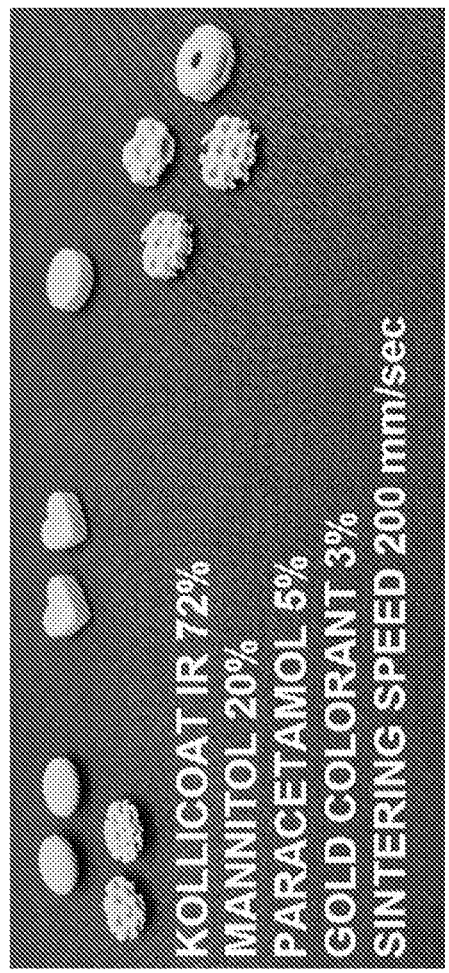
Figure 4 – 3DP geometries from examples

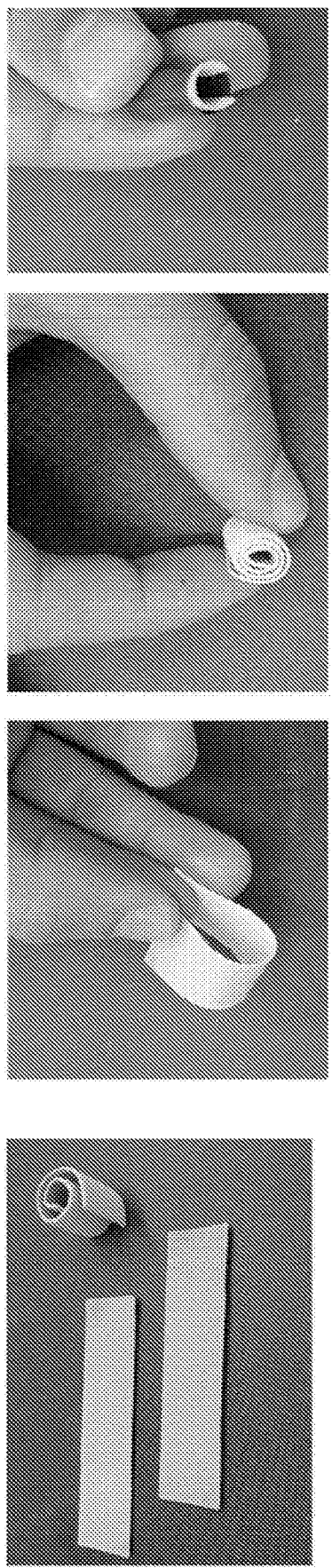
Figure 5 – 3DP geometries from examples

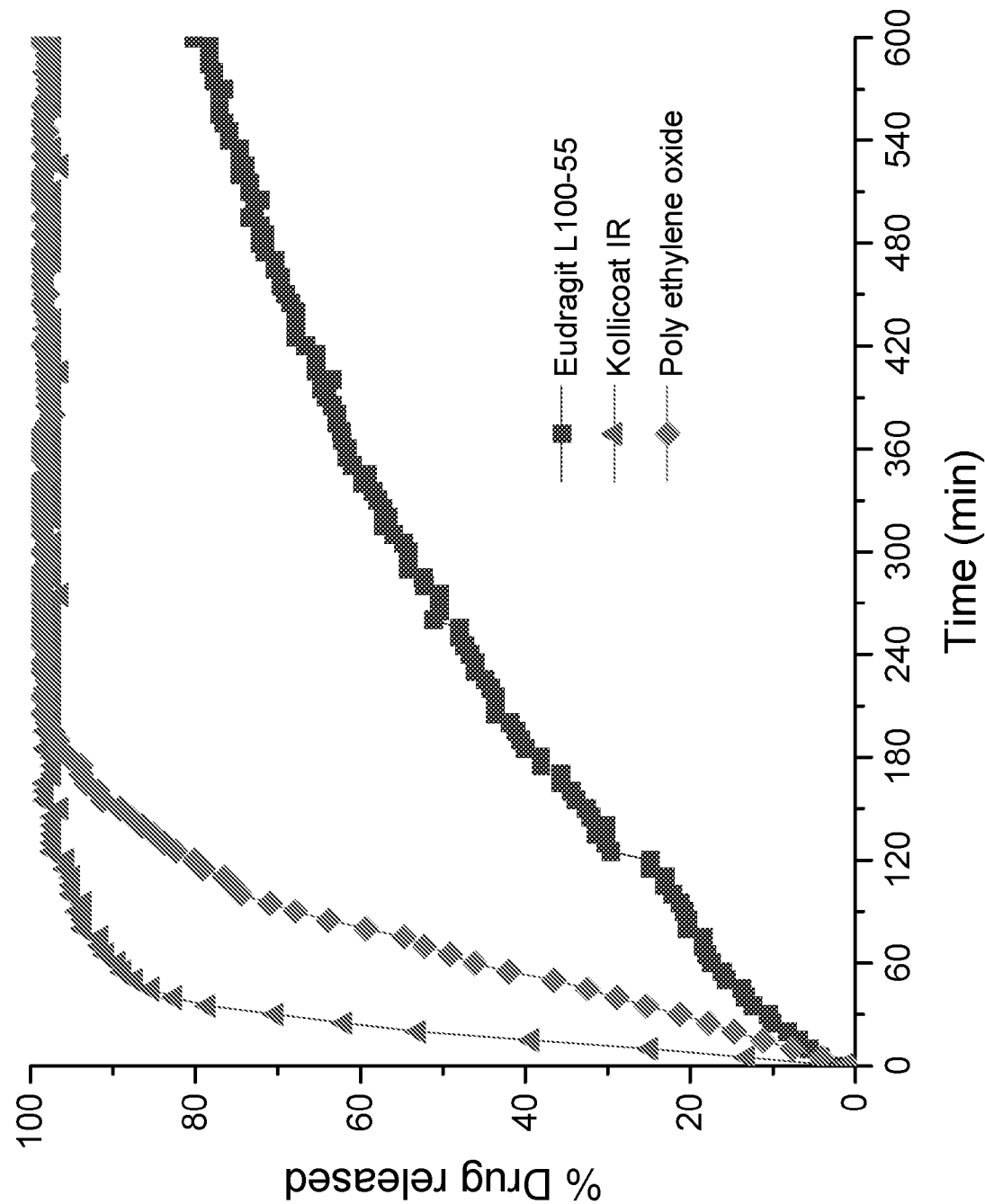
Figure 6 – Drug release of example formulations

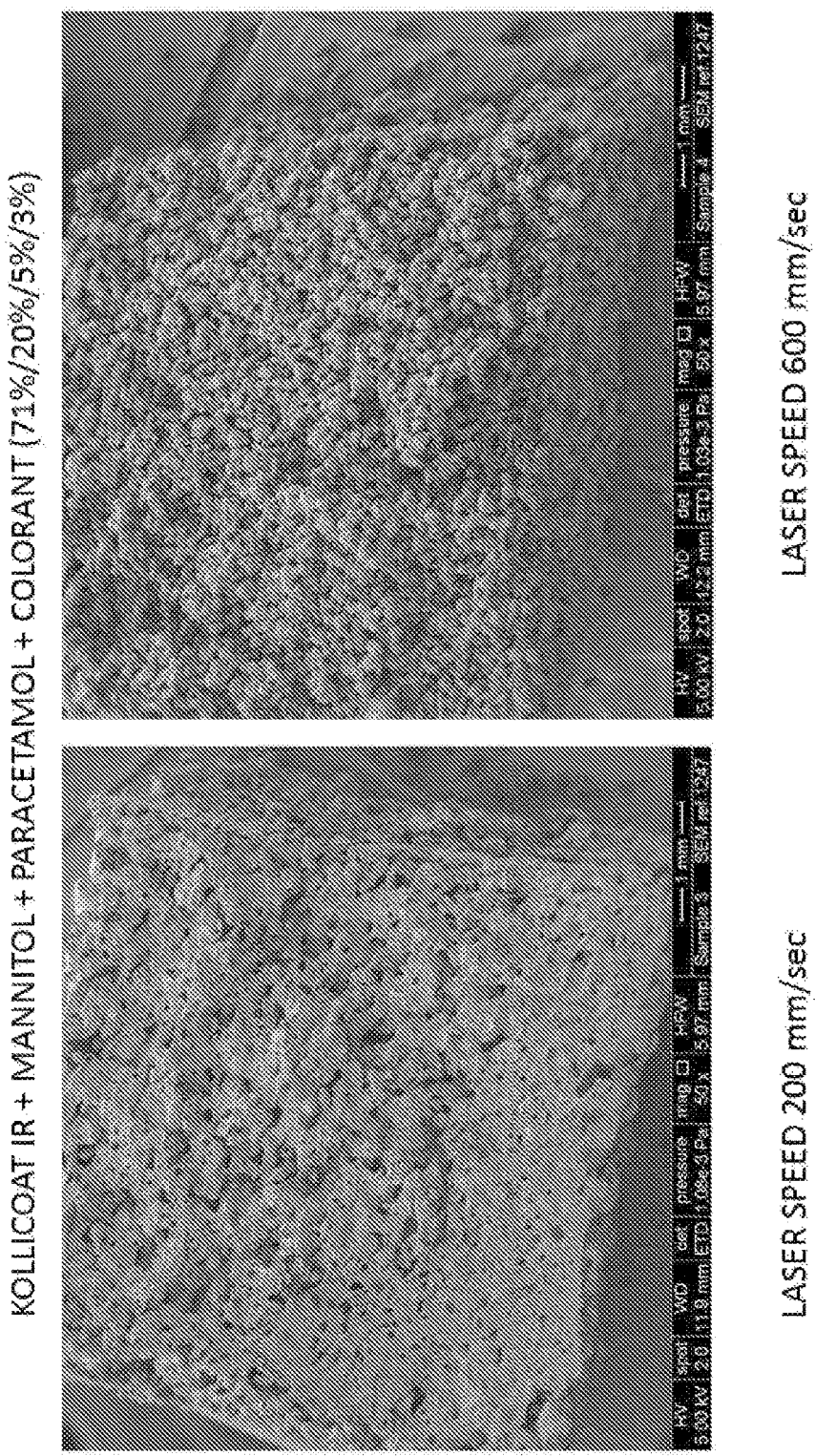
Figure 7 – SEM Micrographs of Kollicoat IR + Mannitol + Paracetamol + Colourant as absorbant material (71%/20%/5%/3%) at different laser scan speeds

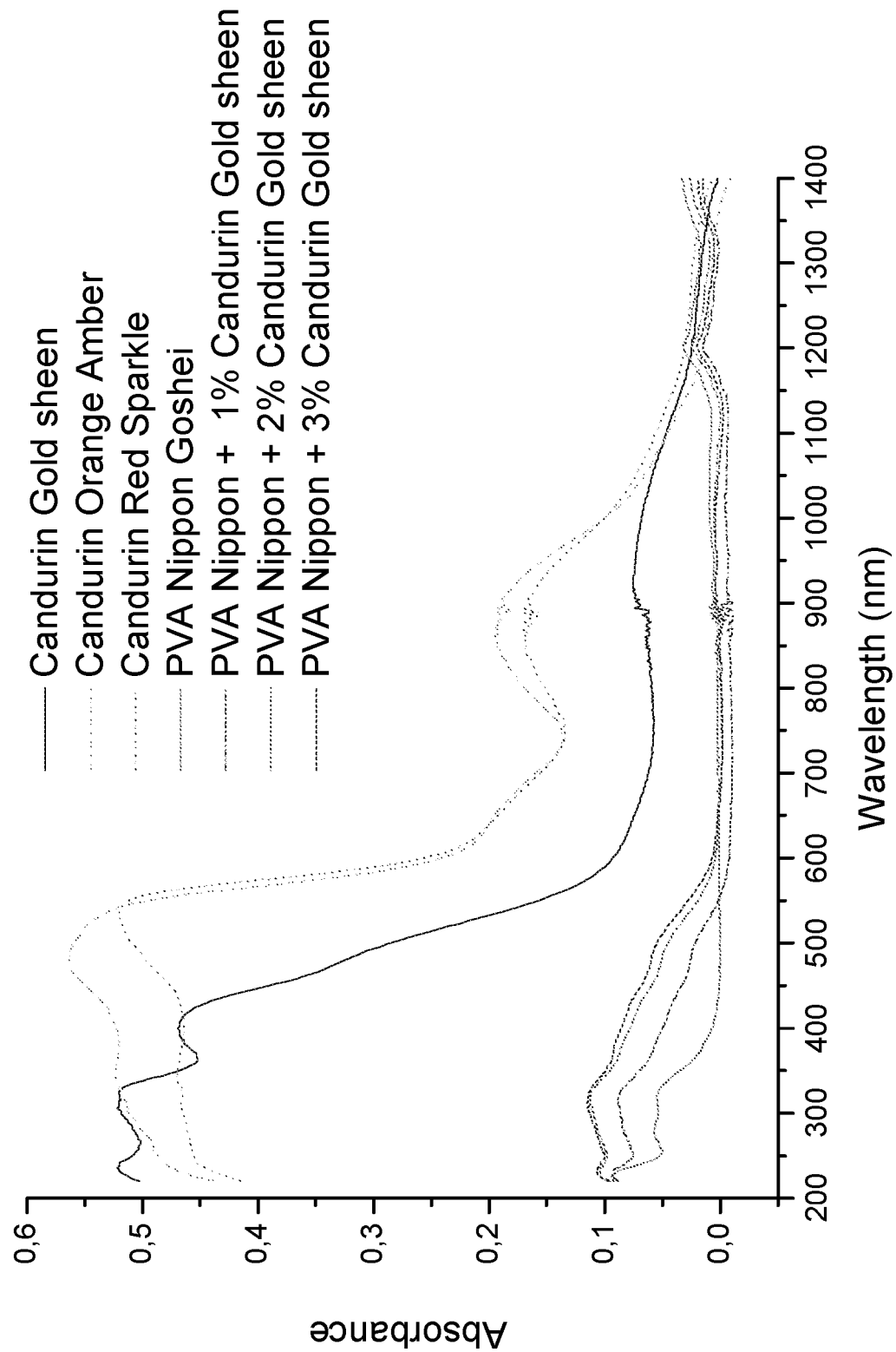
Figure 8 – Cardurin colourants used as absorbent material and PVA polymer absorbance

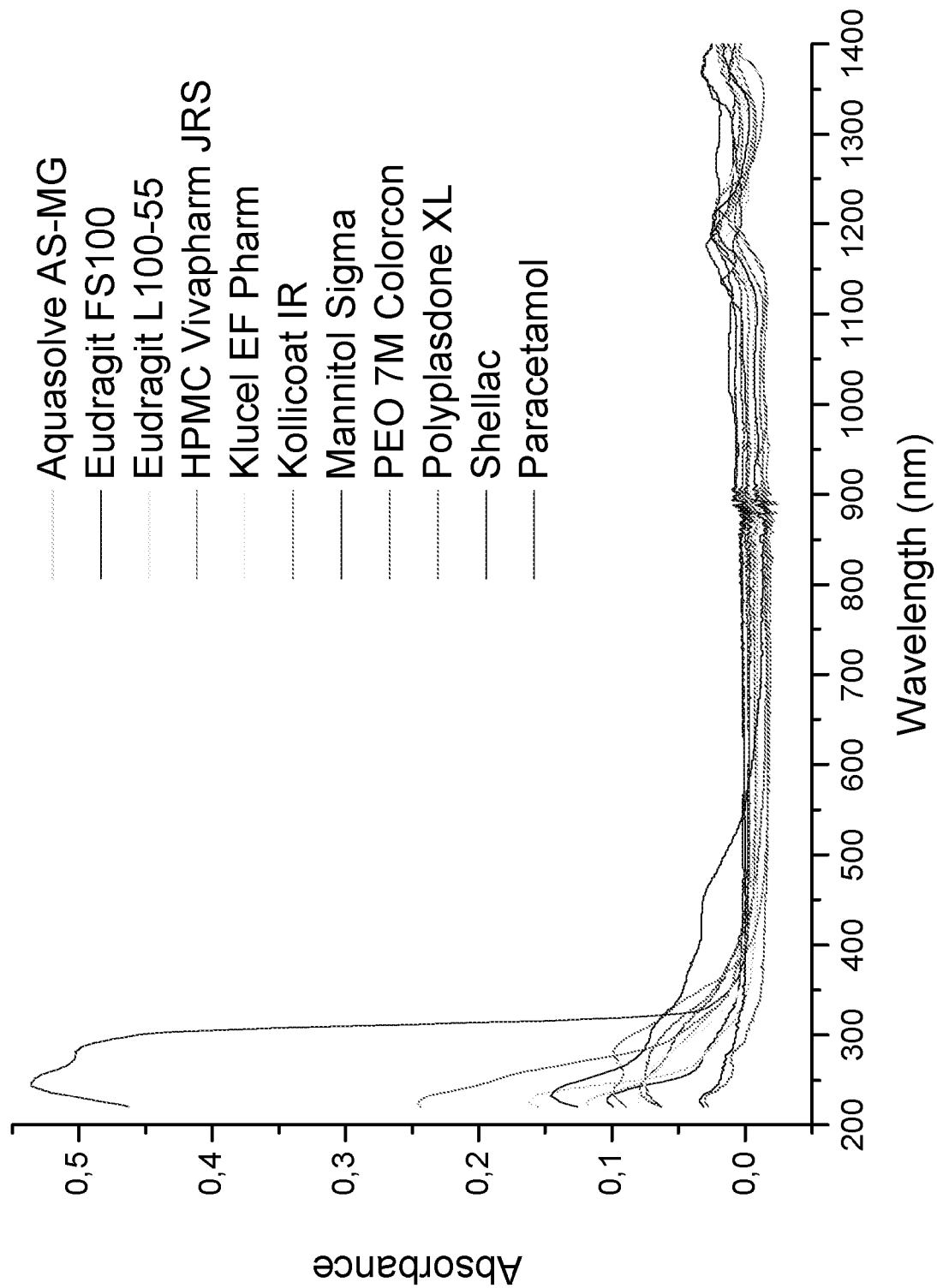
Figure 9 – Absorbance values of some polymers and the drug paracetamol.

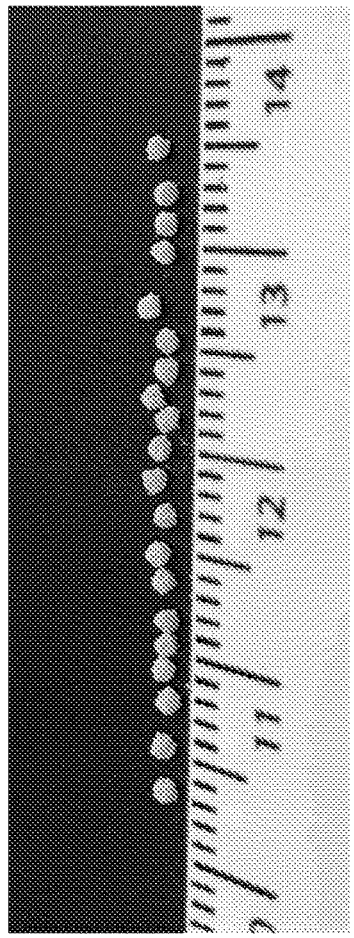
Figure 10 – Kollidon VA-64 0.1mm diameter pellets
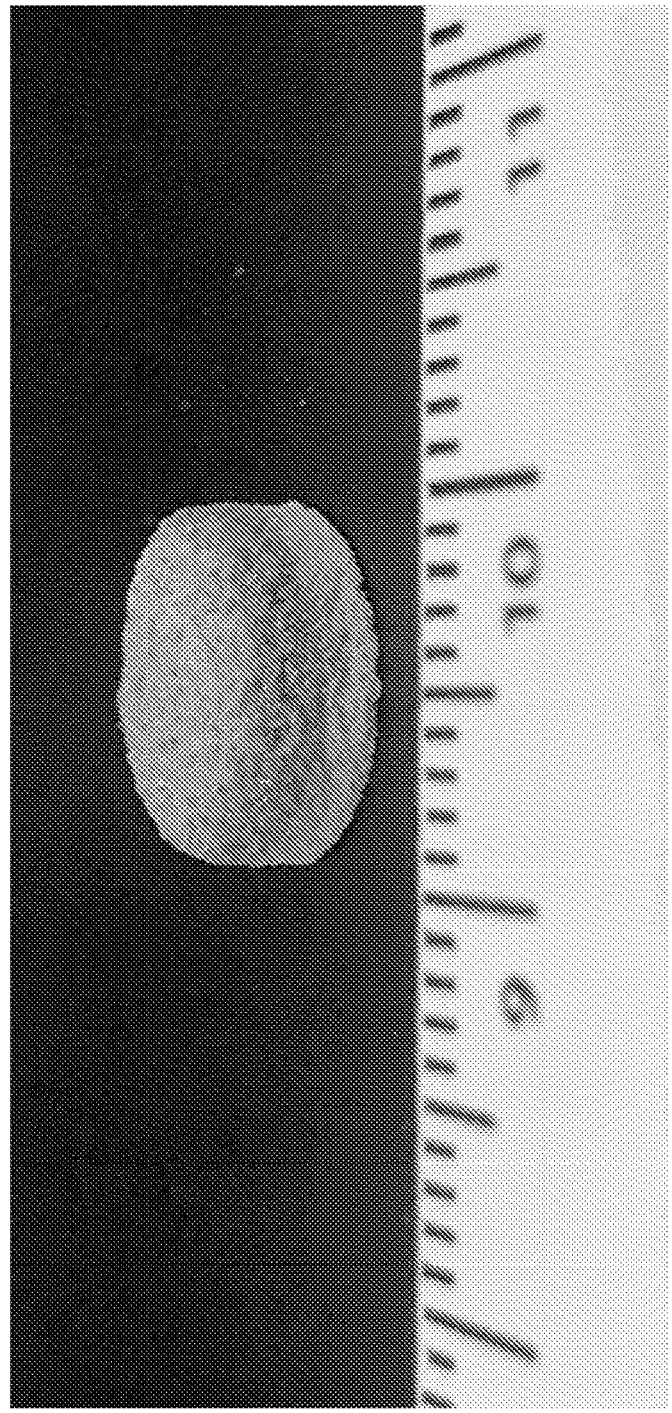
Figure 11 – Polypill containing paracetamol and salicylic acid in two different layers

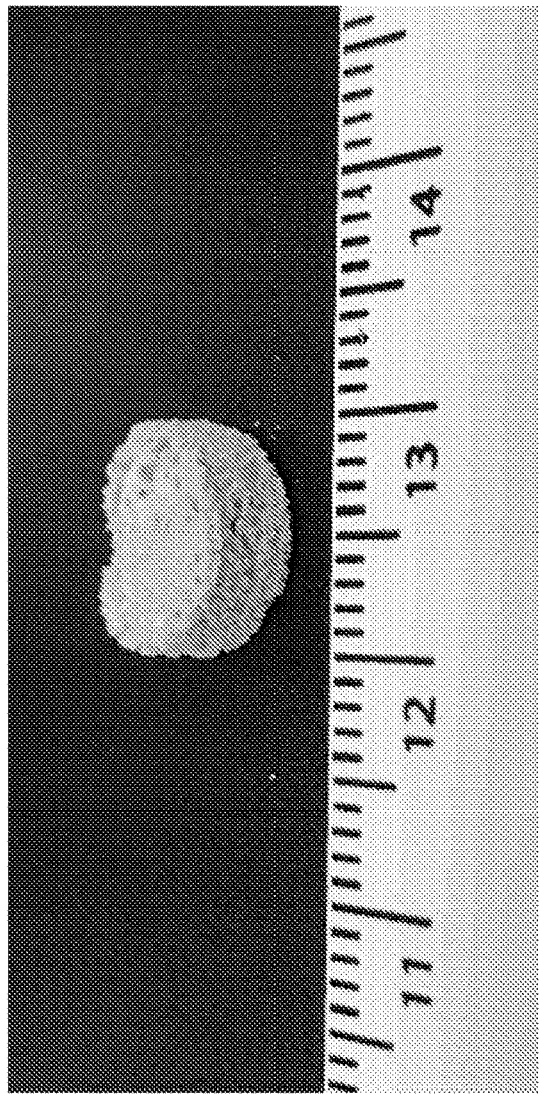
Figure 12 – 80% paracetamol loaded tablet according to example 8
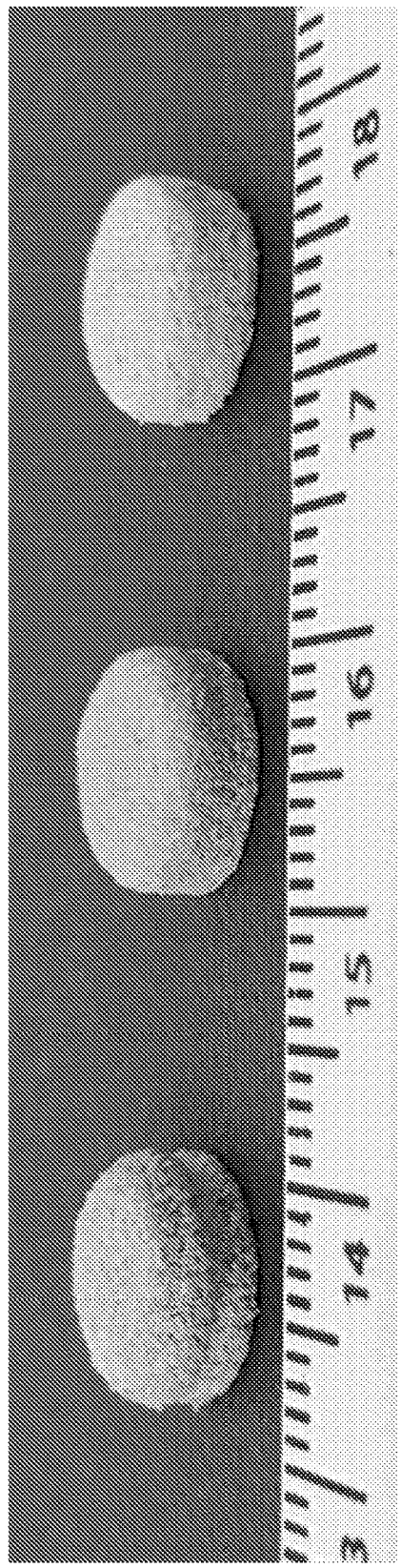
Figure 13: Tablets made of PEO 100KDa containing the drug 4-ASA printed with three different laser scanning speeds. From left to right: 200, 300, 400 mm/s

SOLID PHARMACEUTICAL DOSAGE FORMULATIONS AND PROCESSES

FIELD

The present invention relates to solid pharmaceutical dosage formulations. The invention further relates to methods for the manufacture of such dosage formulations by means of powder bed fusion selective laser 3-dimensional printing.

BACKGROUND

The creation of improved drug formulations, providing improved performance of the drug over a wide range of characteristics (such as bio-availability, taste masking, patient adherence, etc.) is a challenging and competitive area of research, providing a means to optimize clinical performance. Technologies which optimize drug performance offer a means both to improve the chance of efficacy of new drugs in development and are also critical to development of improved formulations of existing drugs, thereby improving clinical outcomes for patients and providing line extension for drug manufacturers.

3-dimensional (3D) printing technology has been exploited in multiple industries in recent years, both as a means to prototype new parts and as a method of manufacture of finished commercial items. It has been utilized in medical applications in areas such as manufacture of bespoke implants and experimentally as a means to create new organs by 3D printing of cell-based structures.

In addition to the potential to improve formulation characteristics, 3D printing has distinct advantages over alternative production methodologies. 3D printing allows the creation of unusual shapes, such as hollow or bi-phasic structures; and it also allow use of different materials and excipients. Perhaps most importantly, however, 3D printing offers a unique means to personalize medicines. It is envisioned that in future, drug prescribing will be dictated by personal characteristics such as age, body-weight, sex and genetics; 3D printing offers a unique means to create drug formulations to order which is not available to alternative production technologies.

3D printing is beginning to be explored as technology for the production of personalized dose medicines and various commercially available 3D printing approaches have been reported to print medicines. The first system used to manufacture 3D printed medicines was based on powder bed-liquid 3D printing technology in the late 1990s, see for example Katstra et a/"Oral dosage forms fabricated by three dimensional printing", *J. Control Release*, 66 (2000), 1-9. Recently the first 3D-printed tablet was approved by the FDA, Spritam® (levetiracetam). ZipDose®, the technology used to print this medicine, is based on powder bed-liquid 3D printing technology where liquid binder is used to fuse together multiple layers of powder to create the tablet.

Alhnan et al. recently reviewed the opportunities and challenges in respect of 3D printed dosage forms (M. A. Alhnan et al., *Pharm. Res.*, 2016 August, 33(8), pp.1817-32, DOI 10.1007/s11095-016-1933-1).

Another 3DP technology, fused-deposition modelling (FDM), has been the subject of recent investigation as a having the most immediate potential to small-scale unit dose fabrication.

The principle underpinning FDM technology is the deposition of thin strands of melted polymer from a filament, creating layers until the desired object is printed.

However, FDM is not suitable for the production of a wide variety of dosage forms, including, for example, films or fast-dissolving tablets such as for sublingual administration. Hence there is a need in the art for a method offering the general advantages of 3D printing but also offering a wider variety of dosage forms, with a wide variety of drugs.

It is an objective of the current invention to provide pharmaceutical dosage forms and methods which overcome the above problems.

The current inventors have now found that powder bed fusion selective laser 3D printing methods can offer much greater versatility in dosage forms. It had been anticipated to be unlikely that this technology could be adapted to successfully print drug formulations, owing to the degradation of excipients or drugs. The current inventors, however, have developed techniques and methods through which is has proved possible to create drug formulations which benefit from the logistical manufacturing attributes of 3D printing outlined above, and which offer unique possibilities for drug administration and performance in vivo.

The methods of the current invention provide for 3D printing using standard excipients which are commonly used in pharmaceutical products. This will allow relatively rapid adoption by the industry. Technically, these methods allow generation of formulations which cannot be generated by standard pharmaceutical manufacturing processes.

For example, the methods of the current invention can provide potential benefit to drug formulations in terms of: the production of tamper-resistant forms for controlled drug substances; the possibility of tapering drug dosage in a personalised fashion to facilitate gradual withdrawal of addictive drugs; the manufacture of high-dose immediate release, rapidly disintegrating tablets; the manufacture of taste masked formulations; and the manufacture of buccal films.

SUMMARY OF INVENTION

In one aspect the current invention provides a process for producing a solid pharmaceutical dosage formulation, said process comprising powder bed fusion selective laser 3-dimensional printing of a mixture comprising:
(a) a drug; and
(b) an excipient;
wherein at least one of said drug and said excipient absorbs electromagnetic radiation at a wavelength emitted by the laser;
or
(a) a drug;
(b) an excipient; and
(c) an absorbent material which absorbs electromagnetic radiation at a wavelength emitted by the laser Preferably the process may have one or all of the following features, or a mixture thereof:
said powder bed fusion selective laser 3-dimensional printing comprises selective laser sintering 3-dimensional printing or selective laser melting 3-dimensional printing, or a mixture thereof, preferably selective laser sintering 3-dimensional printing;
said excipient absorbs electromagnetic radiation at a wavelength emitted by the laser;
said electromagnetic radiation is electromagnetic radiation within the infrared, visible or ultraviolet regions of the electromagnetic spectrum;
the laser power is less than 140 W, preferably less than 7 W, more preferably less than 5 W, for example less than 3

W and/or the laser power is at least 1 W, preferably at least 1.5 W, more preferably at least 2 W;

said mixture is a heterogeneous mixture; the laser emits electromagnetic radiation having a wavelength in the range of from 200 nm to 11 μm, preferably 315 nm to 1.4 μm, more preferably 380 nm to 800 nm, such as 400 nm to 610 nm, preferably 400 nm to 500 nm, more preferably 430 nm to 470 nm;

said solid pharmaceutical dosage formulation is selected from the group consisting of oral formulations, buccal formulations, topical formulations, transdermal formulations, sublingual formulations, enteral formulations, dental formulations, rectal formulations, urethral formulations and vaginal formulations;

said solid pharmaceutical dosage formulation is selected from the group consisting of tablets, caplets, orally-disintegrating tablets, films, masks, and patches;

said solid pharmaceutical dosage formulation is a modified release formulation, immediate release formulation, colonic delivery formulation, enteric formulation, or gastroretentive formulation;

said printing is performed using a scan speed in the range of from 5 mm/s to 50000 mm/s, preferably from 10 mm/s to 1000 mm/s, more preferably from 20 mm/s to 300 mm/s and most preferably from 30 mm/s to 200 mm/s;

said printing is performed using a surface temperature in the range of 0-200° C., preferably 40-180° C., most preferably 70-170° C.;

said mixture comprises from 0.01 wt. % to 85 wt. % of the said drug by total weight of the mixture;

said drug is selected from the group consisting of poorly water-soluble drugs, immunosuppressants, central nervous system drugs, circulatory system drugs, respiratory system drugs, digestive system drugs, antitussive and expectorant drugs, antihistamine drugs, antipyretic, analgesic and anti-inflammatory drugs, diuretic drugs, autonomic drugs, antimalarial drugs, anti-diarrheal drugs, steroids, antineoplastic drugs, psychotropic drugs, proteins, peptides, biological drugs, gastro-intestinal system drugs, cardiovascular system drugs, infection drugs, endocrine system drugs, genitourinary system drugs, malignant disease drugs, blood and nutrition drugs, musculoskeletal system drugs, "eye, ear, nose, and oropharynx" drugs, skin drugs, vaccines, anaesthesia drugs, emergency treatment of poisoning drugs, and vitamins and derivatives thereof; said drug is administrable by at least one of oral administration, buccal administration, topical administration, oral-mucosal administration, transdermal administration, sublingual administration, enteral administration, dental administration, rectal administration, urethral administration and vaginal administration;

said mixture comprises two or more excipients;

said mixture comprises from 15 wt. % to 99.5 wt. % of the said excipients by total weight of the mixture;

the said excipient comprises or consists of a polymer;

said polymer comprises at least one enteric polymer, preferably a pH-dependently soluble enteric polymer having a pH threshold of at least 5; or said polymer comprises at least one pH-independently soluble polymer, preferably which is a rapid-disintegrating polymer or slow release polymer;

said polymer has a glass transition temperature in the range of from −100° C. to 250° C.;

said polymer is selected from the group consisting of acrylic-derived polymers, cellulose-derived polymers and polyvinyl-derived polymers and mixtures thereof;

said polymer is selected from the group consisting of methyl acrylate-methacrylic acid copolymers, ethyl acrylate-methacrylic acid copolymers, cellulose acetate succinate, hydroxy propyl methyl cellulose phthalate, hydroxypropylmethyl cellulose acetate succinate, polyvinyl acetate phthalate, methyl methacrylate-methacrylic acid copolymers, shellac, cellulose acetate trimellitate, sodium alginate, zein, polyethylene oxide, ethylcellulose, hydroxypropyl cellulose, hydroxypropyl methylcellulose, polyvinylpyrrolidone, vinylpyrrolidone-vinyl acetate copolymers, gelatin, polysaccharides and mixtures thereof;

said mixture comprises from 0.1 wt. % to 50 wt. % of the said absorbent material by total weight of the mixture;

said absorbent material is selected from the group consisting of inorganic absorbent materials, aromatic absorbent materials, azo compounds, natural colourants, dyes, pigments, and organic absorbent materials;

said absorbent material comprises iron oxide, titanium oxide, silicates, carmine, candurin, phtalocyanine, diazos, or mixtures thereof.

Preferably said mixture comprises:
(a) 1-50 wt. % of a drug selected from anti-inflammatory, steroid or antineoplastic drugs by total weight of the mixture,
(b) 20-80 wt. % of an enteric polymer selected from methyl acrylate-methacrylic acid copolymers, ethyl acrylate-methacrylic acid copolymers, cellulose acetate succinate, hydroxy propyl methyl cellulose phthalate, hydroxypropylmethyl cellulose acetate succinate, polyvinyl acetate phthalate, methyl methacrylate-methacrylic acid copolymers, shellac, cellulose acetate trimellitate, sodium alginate, zein, polyethylene oxide, ethylcellulose, hydroxypropyl cellulose, hydroxypropyl methylcellulose, polyvinylpyrrolidone, vinylpyrrolidone-vinyl acetate copolymers, gelatin, and mixtures thereof, by total weight of the mixture; and
(c) 0.1-30 wt. % of at least one absorbent material selected from iron oxide, titanium oxide, silicates, carmine, candurin, phthalocyanine, diazos or mixtures thereof, by total weight of the mixture.

Preferably the said mixture is ground before undergoing printing, preferably to a particle size of less than 500 μm, preferably from 1 μm to 100 μm, more preferably 10-50 μm.

Preferably the chamber temperature of the 3-dimensional printer is in the range 25-200° C., preferably 60-150° C.;

said printing is performed with a layer height setting in the range of 0.0025 mm to 0.5 mm;

said printing is performed using a beam spot size from 0.0025 mm to 1 mm, preferably 0.05 mm to 0.5 mm, more preferably 0.1 to 0.3 mm, for example 0.2 mm.

In another aspect, the invention provides a solid pharmaceutical dosage formulation produced by the process of the invention.

Preferably said solid pharmaceutical dosage formulation is an oral dosage formulation, a buccal dosage formulation, a topical dosage formulation, a transdermal dosage formulation, a sublingual formulation, an enteral formulation, a dental formulation, a rectal formulation, a urethral formulation, paediatric formulation, oral-mucosal formulations, oral disintegrating formulation, formulation for dispersion or a vaginal formulation.

Preferably said solid pharmaceutical dosage formulation is bioadhesive and/or mucoadhesive.

In yet another aspect, the invention provides a solid pharmaceutical dosage formulation, the surface of which comprises a drug and a sintered polymer and/or sintered absorbent material.

Preferably said solid pharmaceutical dosage formulation is an oral dosage formulation, a buccal dosage formulation, a topical dosage formulation, a transdermal dosage formulation, a sublingual formulation, an enteral formulation, a dental formulation, a rectal formulation, a urethral formulation, paediatric formulation, oral-mucosal formulations, oral disintegrating formulation, formulation for dispersion or a vaginal formulation.

Preferably in said solid pharmaceutical dosage formulation said drug is suspended in a matrix comprising:
(a) An excipient which absorbs electromagnetic radiation at a wavelength of 200 nm to 11 µm, preferably 315 nm to 1.4 µm, more preferably 380 nm to 800 nm, preferably 400 nm to 610 nm;
or
(a) an excipient; and
(b) an absorbent material which absorbs electromagnetic radiation at a wavelength of 200 nm to 11 µm, preferably 315 nm to 1.4 µm, more preferably 380 nm to 800 nm, preferably 400 nm to 610 nm.

Preferably in the solid pharmaceutical dosage formulations of the invention, said drug, said excipient and/or said absorbent material are as previously defined with respect to the process of the invention.

Preferably the solid pharmaceutical dosage formulations of the invention have a laminated core comprising multiple layers, each layer comprising:
(a) a drug,
(b) an excipient, and
(c) optionally an absorbent material.

Preferably the average thickness of each layer in the laminated core is in the range from 0.01 mm to 10 mm, preferably 0.01 mm to 0.5 mm.

DETAILED DESCRIPTION

General Definitions

Throughout this application terms should be interpreted according to their standard meaning in the art unless specified otherwise. The following terms should be construed according to their standard meanings, as set out below.

As used in this specification and the appended claims, the singular forms "a", "an", and "the" include plural references unless the context clearly dictates otherwise. Thus for example, a reference to "a method" includes one or more methods, and/or steps of the type described herein and/or which will become apparent to those persons skilled in the art upon reading this disclosure and so forth.

The term "approximately" or "about" in connection with a number is intended to mean "in the region of", i.e. within normal tolerance of the stated value. In other words, a value that the skilled worker in the relevant field would round up or round down to reach the "approximate" value. For example a value in the range of 95 to 104 would be "approximately 100", or 0.96 to 1.04 would be "approximately 1".

The term "at least" when used in connection with a number has its standard meaning, i.e. means that number is the minimum value for the specified parameter/component. For example "at least one polymer" means there is one or more polymer and discloses the options of one polymer or more than one polymer being present.

The term "comprising" should be construed as meaning "including but not limited to". The term "comprising" also discloses mixtures, processes and the like "consisting essentially of" the specified features and "consisting of" the specified features. For example, a mixture disclosed herein as comprising components (a) to (d) also discloses a mixture consisting of components (a) to (d).

The term "excipient" means a pharmacologically inactive component such as a diluent, disintegrant, carrier, etc of a pharmaceutical product. The excipients that are useful in preparing a pharmaceutical composition are generally safe, non-toxic and are acceptable for veterinary as well as human pharmaceutical use. Reference to an excipient includes both one and more than one such excipient. The term "composition" or "pharmaceutical composition" or "solid oral composition" or "oral dosage form" as used herein synonymously include solid dosage forms such as tablets, capsules, granules, mini-tablets and the like meant for oral administration.

The term "greater than" when used in connection with a number has its standard meaning, i.e. means that the specified parameter has a value higher than the specified number.

The term "not greater than" or "no more than" when used in connection with a number has its standard meaning, i.e. means that the specified parameter has a maximum value equal to the specified number.

The term "in the range from X to Y" has its standard meaning, i.e. the value of the parameter is a minimum of X and a maximum of Y.

The term "less than" when used in connection with a number has its standard meaning, i.e. means that the specified parameter has a value lower than the specified number.

The term "multiple" has its standard meaning, i.e. at least 2, more preferably at least 3.

The term "no less than" or "not less than" when used in connection with a number has its standard meaning, i.e. means that the specified parameter has a minimum value equal to the specified number.

The term "optionally" has its standard meaning, i.e. means that the specified feature is not essential and may or may not be present. Optional components or process steps disclose the claimed product or process including and not including the optional feature.

The term "performed using" as for example in "3D printing is performed using" has its standard meaning, i.e. when the claimed process is carried out, the specified feature applies.

The term "pharmaceutical grade" has its standard meaning of being suitable for use in pharmaceutical products. For example, the product may be in excess of 80% purity, preferably 90% purity, more preferably 95% purity, even more preferably 99% purity. Optionally "pharmaceutical grade products" may be products that are more than 99% pure and without binders, fillers, excipients, dyes, or unknown substances.

The term "solid" throughout this application is used to refer to the state of matter, i.e. to distinguish from liquids and gels.

The term "weight %" or "percent by weight" has its standard meaning throughout this application, i.e. percentage by weight based on the total weight of the relevant mixture. In other words the total weight of the mixture is 100%.

Features which are described herein with reference only to a single aspect or embodiment of the invention apply equally to all other aspects and embodiments of the invention. Hence features from one aspect or embodiment may be combined with features from another aspect or embodiment. For example, the disclosed drugs, excipients and absorbent materials may be combined in any way with each other and with the disclosed features of the powder bed fusion selective laser 3D printing processes.

Component Materials

For all aspects and embodiments of the invention the component materials used are pharmaceutical-grade, in order to provide end products which are suitable for the administration of drugs.

The drugs, excipients and absorbent materials suitable for use in the aspects and embodiments of the invention are described hereinafter individually. The skilled worker will readily understand that each component can be combined with the other components described and such combinations are applicable to all aspects and embodiments of the invention.

Drugs

The drug is not particularly limited insofar as it is administrable by at least one of oral administration, buccal administration, topical administration, transdermal administration, sublingual administration, enteral administration, dental administration, rectal administration, urethral administration and vaginal administration.

In a preferred embodiment applicable to all aspects of the invention, the drug is administrable orally, buccally, topically or transdermally. Most preferably the drug is orally or buccally administrable.

Examples of suitable drugs include poorly water-soluble drugs, immunosuppressants, central nervous system drugs, circulatory system drugs, respiratory system drugs, digestive system drugs, antitussive and expectorant drugs, antihistamine drugs, antipyretic, analgesic and anti-inflammatory drugs, diuretic drugs, autonomic drugs, antimalarial drugs, anti-diarrheal drugs, steroids, antineoplastic drugs, psychotropic drugs, proteins, peptides, biological drugs, gastrointestinal system drugs, cardiovascular system drugs, infection drugs, endocrine system drugs, genito-urinary system drugs, malignant disease drugs, blood and nutrition drugs, musculoskeletal system drugs, "eye, ear, nose, and oropharynx" drugs, skin drugs, vaccines, anaesthesia drugs, emergency treatment of poisoning drugs, and vitamins and derivatives thereof.

Alternative terminology refers to "medicament", "active ingredient" or "active agent" instead of "drug". For the avoidance of doubt, these terms are used synonymously herein.

Preferably the drug is selected from anti-inflammatory drugs, immunosuppressants, steroids, and antineoplastic drugs. More preferably, from anti-inflammatory drugs, steroids, and antineoplastic drugs Examples of poorly water-soluble drugs include azole-based compounds such as itraconazole, ketoconazole, fluconazole and mitoconazole; dihydropyridine-based compounds such as nifedipine, nitrendipine, amlodipine, nicardipine, nilvadipine, felodipine and efonidipine; propionic acid-based compounds such as ibuprofen, ketoprofen and naproxen; and indoleacetic acid-based compounds such as indomethacin and acemetacin. Additional examples include griseofulvin, phenytoin, carbamazepine and dipypridamole.

Examples of immunosuppressants include azathioprine; cyclosporin; and methotrexate.

Examples of the central nervous system drugs include diazepam, idebenone, aspirin, ibuprofen, paracetamol, naproxen, piroxicam, diclofenac, indomethacin, sunlindac, lorazepam, nitrazepam, phenytoin, acetaminophen, ethenzamide, ketoprofen and chlordiazepoxide.

Examples of the circulatory system drugs include molsidomine, vinpocetine, propranolol, methyldopa, dipyridamole, furosemide, triamterene, nifedipine, atenolol, spironolactone, metoprolol, pindolol, captopril, isosorbide nitrate, delapril hydrochloride, meclofenoxate hydrochloride, diltiazem hydrochloride, etilefrine hydrochloride, digitoxin, propranolol hydrochloride and alprenolol hydrochloride.

Examples of the respiratory system drugs include amlexanox, dextromethorphan, theophylline, pseudoephedrine, salbutamol and guaifenesin.

Examples of the digestive system drugs include benzimidazole-based drugs having an anti-ulcer action such as 2-[[3-methyl-4-(2,2,2-trifluoroethoxy)-2-pyridyl]methyl-sulfinyl]benzimidazole and 5-methoxy-2-[(4-methoxy-3,5-dimethyl-2-pyridyl)methylsulfinyl]benzimidazole; cimetidine; ranitidine; pirenzepine hydrochloride; pancreatin; bisacodyl; and 5-aminosalicylic acid.

Examples of the antitussive and expectorant drugs include noscapine hydrochloride, carbetapentane citrate, dextromethorphan hydrobromide, isoaminile citrate and dimemorfan phosphate.

Examples of the antihistamine drugs include chlorpheniramine maleate, diphenhydramine hydrochloride and promethazine hydrochloride.

Examples of the antipyretic, analgesic and anti-inflammatory drugs include ibuprofen, diclofenac sodium, flufenamic acid, sulpyrine, aspirin, ketoprofen, 5ASA (otherwise known as mesalazine or mesalamine), 4ASA, sulphasalazine, and balsalazide.

Examples of the diuretic drugs include caffeine.

Examples of the autonomic drugs include dihydrocodeine phosphate, dl-methylephedrine hydrochloride, propranolol hydrochloride, atropine sulfate, acetylcholine chloride and neostigmine.

Examples of the antimalarial drugs include quinine hydrochloride.

Examples of the anti-diarrheal drugs include loperamide hydrochloride.

Examples of the steroid drugs include prednisolone, budesonide and fluticasone.

Examples of the antineoplastic drugs include fluorouracil; methotrexate; dactinomycin; bleomycin; etoposide; taxol; vincristine; doxorubicin; cisplatin; daunorubicin; VP-16; raltitrexed; oxaliplatin; and pharmacologically acceptable derivatives and salts thereof.

Examples of the psychotropic drugs include chlorpromazine.

Examples of the vitamins and derivatives thereof include Vitamin A, Vitamin B1, fursultiamine, Vitamin B2, Vitamin B6, Vitamin B12, Vitamin C, Vitamin D, Vitamin E, Vitamin K, calcium pantothenate and tranexamic acid.

Examples of proteins and peptides include erythropoietin, a glycosylated protein hormone and haematopoietic growth factor, which is considered useful in the management of anaemia in chronic renal failure among other conditions and has been investigated in the treatment of anaemia of inflammatory bowel disease as well as other normocytic-normochromic anaemias. Erythropoietin is conventionally administered subcutaneously or intravenously, although a tabletted form of erythropoietin has been disclosed (RU-A-2152206).

Other examples include interferons, TNF antagonists and specific protein and polypeptide agonists and antagonists of the immune system, hormones, such as human growth hormone and cytokines and cytokine antagonists. Other high molecular weight compounds that might be used include vaccines.

Examples of biological drugs include: blood factors, such as Factor VIII and Factor IX; thrombolytic agents such as tissue plasminogen activator; hormones such as insulin, glucagon, growth hormone and gonadotrophins; haematopoietic growth factors such as erythropoietin, colony stimulating factors; interferons such as -α. -β, and -γ; interleukin-based products such as interleukin-2; vaccines such as hepatitis B surface antigen; monoclonal antibodies; tumour necrosis factor; and therapeutic enzymes.

Preferred proteins, peptides and biological drugs include: abatacept, adalimumab, alefacept, erythropoietin, etanercept, infliximab, trastuzumab, ustekinumab, denileukin difitox, and golimumab.

Examples of gastro-intestinal system drugs include: atropine, aminosalicylates (balsalazide sodium, mesalazine, olsalazine sodium, and sulfasalazine and the like), corticosteroids (such as hydrocortisone, beclometasone dipropionate, budesonide, and prednisolone and the like), and sodium cromoglicate.

Examples of cardiovascular system drugs include: nifedipine, diltiazem, verapamil, clopidogrel, digoxin, warfarin, acenocoumarol, and phenindione.

Examples of infection drugs include: lopinavir, ritonavir, nevirapine, rilpivirine, acyclovir, metronidazole, isoniazid, rifampicin, entecavir, and sofosbuvir.

Examples of endocrine system drugs include: orlistat, carbimazole, levothyroxine, propranolol, and clonidine.

Examples of genito-urinary system drugs include: chlorhexidine, epirubicin, doxorubicin, oxybutynin, tolterodine, solifenacin, dutasteride, and finasteride.

Examples of malignant disease drugs include: fluorouracil, etoposide, methotrexate, cyclophosphamide, mitoxantrone, cisplatin, dacarbazine, and paclitaxel.

Examples of blood and nutrition drugs include: magnesium sulfate, lanthanum, and vitamins.

Examples of musculoskeletal system drugs include: azathioprine, ciclosporin, cyclophosphamide, leflunomide, penicillamine, gold, quinine, and glyceryl trinitrate.

Examples of "eye, ear, nose, and oropharynx" drugs include: Montelukast and Ephedrine.

Examples of skin drugs include: pimecrolimus, metformin and tacrolimus.

Examples of vaccines include: immunoglobulin, live attenuated form of a virus or bacteria, inactivated preparations of the virus or bacteria, detoxified exotoxins produced by a micro-organism, and extracts of a micro-organism.

Examples of emergency treatment of poisoning drugs include: glyceryl trinitrate, Metoclopramide hydrochloride, diazepam, and activated charcoal.

Pharmacologically acceptable derivatives and/or salts of the drugs may also be used in the formulations. An example of a suitable salt of prednisolone is methyl prednisolone sodium succinate. A further example is fluticasone propionate.

Preferably the drug is selected from the group of anti-inflammatory drugs, immunosuppressants, steroids, and antineoplastic drugs consisting of: ibuprofen, diclofenac sodium, 5ASA (otherwise known as mesalazine or mesalamine), 4ASA, sulphasalazine, and balsalazide; azathioprine, cyclosporin, and methotrexate; prednisolone, budesonide and fluticasone; fluorouracil, methotrexate, dactinomycin, bleomycin, etoposide, taxol, vincristine, doxorubicin, cisplatin, daunorubicin, VP-16, raltitrexed, oxaliplatin; and pharmacologically acceptable derivatives and salts thereof.

More preferably, the drug is selected from anti-inflammatory drugs, steroids, and antineoplastic drugs selected from the group consisting of: ibuprofen, diclofenac sodium, 5ASA (otherwise known as mesalazine or mesalamine), 4ASA, sulphasalazine, and balsalazide; prednisolone, budesonide and fluticasone; fluorouracil, methotrexate, dactinomycin, bleomycin, etoposide, taxol, vincristine, doxorubicin, cisplatin, daunorubicin, VP-16, raltitrexed, oxaliplatin; and pharmacologically acceptable derivatives and salts thereof.

In one embodiment, applicable to all aspects of the invention, the at least one drug does not include antibiotics.

The formulations of the invention will typically comprise a therapeutically effective amount of the or each drug which may be from about 0.01 wt.,% to about 99.5 wt.,%, based on the total weight of the formulation. The actual dosage would be determined by the skilled person using their common general knowledge. However, by way of example, "low" dose formulations typically comprise no more than about 20 wt. % of the drug, and preferably comprise from about 1 wt. % to about 10 wt. %, e.g. about 5 wt. %, of the drug. "High" dose formulations typically comprise at least 40 wt. % of the drug, and preferably from about 45 wt. % to about 85 wt. %, e.g. about 50 wt. % or about 80 wt. %.

Preferably the solid pharmaceutical dosage formulation is a "low" dose formulation.

In the initial mixture the drug may be present in an amount which may be from about 0.01 wt.,% to about 99.5 wt.,%, based on the total weight of the mixture. The actual dosage would be determined by the skilled person using his common general knowledge. For a "low" dose formulation, initial mixtures typically comprise no more than about 25 wt. % of the drug, and preferably comprise from about 1 wt. % to about 15 wt. %, e.g. about 5 wt. %, of the drug. For a "high" dose formulation, initial mixtures typically comprise at least 45 wt. % of the drug, and preferably from about 45 wt. % to about 85 wt. %, e.g. about 50 wt. % or about 80 wt. %.

Preferably the amount of drug in the initial mixture corresponds to the amount of drug in the final solid pharmaceutical dosage formulation, in terms of wt. %. Preferably not more than 10 wt. %, more preferably not more than 5 wt. %, even more preferably not more than 2 wt. % and most preferably less than 1 wt. % of the drug is lost during processing.

The drug may preferably be present in the initial mixture in an amount in the range of 0.01 wt. % to 85 wt. %, for example 0.01 to 80 wt. % or 0.1 wt. % to 60 wt. %. More preferably the drug is present in the mixture in an amount in the range of 1 wt. % to 49 wt. %, typical ranges include 2 wt. % to 35 wt. %, 3 wt. % to 25 wt. %. Even more preferred is a range of 1 wt. % to 15 wt. %, e.g. about 5 wt. % or about 10 wt. %. A preferred "high" dose range is 65-85 wt. %, for example 70-80 wt. %.

A preferred combination, applicable to all aspects of the invention is 1 wt. % to 15 wt. %, more preferably 3 wt. % to 10 wt. % of at least one drug selected from the group of anti-inflammatory drugs, immunosuppressants, steroids, and antineoplastic drugs consisting of: ibuprofen, diclofenac sodium, 5ASA (otherwise known as mesalazine or mesalamine), 4ASA, sulphasalazine, and balsalazide; azathioprine, cyclosporin, and methotrexate;

prednisolone, budesonide and fluticasone; fluorouracil, methotrexate, dactinomycin, bleomycin, etoposide, taxol, vincristine, doxorubicin, cisplatin, daunorubicin, VP-16, raltitrexed, oxaliplatin; and pharmacologically acceptable derivatives and salts thereof.

Another combination, preferred for "high" dose formulations and applicable to all aspects of the invention is 65-85 wt. % of at least one drug, preferably selected from the group of anti-inflammatory drugs, immunosuppressants, steroids, and antineoplastic drugs consisting of: ibuprofen, diclofenac sodium, 5ASA (otherwise known as mesalazine or mesalamine), 4ASA, sulphasalazine, and balsalazide;

azathioprine, cyclosporin, and methotrexate; prednisolone, budesonide and fluticasone; fluorouracil, methotrexate, dactinomycin, bleomycin, etoposide, taxol, vincristine, doxorubicin, cisplatin, daunorubicin, VP-16, raltitrexed, oxaliplatin; and pharmacologically acceptable derivatives and salts thereof.

Excipients

In the context of this invention the term "excipient" has its standard meaning in the art, i.e. a substance formulated alongside the active ingredient of a medication, included for the purpose of long-term stabilization, bulking up solid formulations that contain potent active ingredients, or to confer a therapeutic enhancement on the active ingredient in the final dosage form, such as facilitating drug absorption, reducing viscosity, or enhancing solubility.

In addition to transporting the active drug to the site in the body where the drug is intended to exert its action, excipients play an important part in the manufacturing process. They may also be important for keeping the drug from being released too early in the assimilation process in places where it could damage tender tissue and create gastric irritation or stomach upset.

Other excipients help the drug to disintegrate into particles small enough to reach the blood stream more quickly and still others protect the product's stability so it will be at maximum effectiveness at time of use. In addition, some excipients are used to aid the identification of a drug product.

Last, but not least, some excipients are used simply to make the product taste and look better. This improves patient compliance, especially in children. Although technically "inactive" from a therapeutic sense, pharmaceutical excipients are critical and essential components of a modern drug product. In many products, excipients make up the bulk of the total dosage form.

Suitable excipients include diluents or fillers, binders, disintegrants, colouring agents, preservatives, plasticizers, and lubricants.

Without being bound by theory, it is believed to be the excipient or combination of excipients which have the greatest impact upon release of the drug, for example in the digestive system, by means of its dissolution properties e.g. under the conditions found in the stomach and intestine.

Selection of the excipient(s) is therefore influenced by the drug used and the release-behaviour desired in the end-product solid pharmaceutical dosage formulations.

An "orally disintegrating tablet" or orally dissolving tablet" (ODT) is a drug dosage form that differ from traditional tablets in that they are designed to be dissolved on the tongue rather than swallowed whole. The ODT serves as an alternative dosage form for patients who experience dysphagia (difficulty in swallowing) or for where compliance is a known issue and therefore an easier dosage form to take ensures that medication is taken. ODTs also have a faster onset of effects than tablets or capsules, and have the convenience of a tablet that can be taken without water.

"Immediate-release" is the term generally applied to solid pharmaceutical dosage formulations, such as tablets and caplets, which disintegrate rapidly and get dissolved to release the drug. Immediate-release may be provided for by way of an appropriately pharmaceutically acceptable diluent or carrier which does not prolong, to an appreciable extent, the rate of drug-release and/or absorption. This term excludes formulations which are adapted to provide for "modified", "controlled", "sustained", "prolonged", "extended" or "delayed" release of drug.

For immediate-release in oral dosage formulations, the release is under pH conditions such as pH=1-3, especially at or about pH=1. Immediate-release formulations may release at least 70%, preferably 80%, of the drug within 4 hours, such as within 3 hours, preferably 2 hours, more preferably within 1.5 hours, and especially within an hour (such as within 30 minutes) of oral administration. As such, immediate-release formulations typically may be described as having a "burst effect", i.e. the majority, for example 90-100%, of the drug is released within the first hour after application.

"Controlled-release", also referred to as "modified-release", is a term used to describe drug-release where the release does not occur immediately, i.e. is not "immediate-release" as set out above. Throughout this application the terms "controlled-release" and "modified-release" are used synonymously.

In controlled-release there is no "burst effect". Controlled-release formulations include formulations which exhibit sustained-release (also referred to as extended-release), delayed-release such as time-delayed-release and pH-triggered-release, or site-specific-release such as enteric release i.e. intestinal-specific-release, properties. For example, the US Pharmacopeia defines delayed-release formulations as providing less than 10% drug-release during the first two hours in pH 1.2 conditions.

For immediate-release, polymer excipients such as polyvinyl-based polymers may be effective.

For controlled-release, such as site-specific intestinal release or sustained release, a wide range of enteric polymer excipients used to manufacture oral solid dosage forms are already on the market.

In a preferred embodiment, applicable to all aspects of the invention, the excipient comprises or consists of a polymer.

A wide range of polymer excipients used to manufacture solid pharmaceutical dosage forms is already on the market. These include, for example, polymethacrylate polymers, cellulosic polymers and polyvinyl-based polymers. The terms "polymer" and "polymeric materials" are used herein interchangeably.

In a preferred embodiment, applicable to all aspects of the invention, the excipient comprises a polymeric material that dissolves in a pH dependent manner. Such a polymer is pH sensitive, i.e. has a "pH threshold" which is the pH below which it is insoluble in aqueous media and at or above which it is soluble in aqueous media. Thus, the pH of the surrounding medium triggers dissolution of the polymeric material and none (or essentially none) of the polymeric material dissolves below the pH threshold. Once the pH of the surrounding medium reaches (or exceeds) the pH threshold, the polymeric material becomes soluble.

Throughout the specification, the term "insoluble" is used to mean that 1 g of a polymeric material requires more than 10,000 ml of solvent or "surrounding medium" to dissolve at a given pH. In addition, the term "soluble" is used to mean that 1 g of a polymeric material requires less than 10,000 ml, preferably less than 5,000 ml, more preferably less than 1000 ml, even more preferably less than 100 ml or 10 ml of solvent or surrounding medium to dissolve at a given pH.

By "surrounding medium", the inventors mean gastric fluid and intestinal fluid, or an aqueous solution designed to recreate in vitro gastric fluid or intestinal fluid.

The normal pH of gastric juice is usually in the range of pH 1 to 3. Preferably the polymer used according to the invention is insoluble below pH 5 and soluble at about pH 5 or above and, thus, is usually insoluble in gastric juice.

Such a material may be referred to as a gastro-resistant material or an "enteric" material.

The polymer thus preferably has a pH threshold of pH 5 or above, e.g. about pH 5.5 or above, preferably about pH 6 or above and more preferably about pH 6.5 or above. The polymer typically has a pH threshold of no more than about pH 8, e.g. no more than about pH 7.5 and preferably no more than about pH 7.2. Preferably, the polymer has a pH threshold within the range of pH found in intestinal fluid. The pH of intestinal fluid may vary from one person to the next, but in healthy humans is generally from about pH 5 to 6 in the duodenum, from about 6 to 8 in the jejunum, from about 7 to 8 in the ileum, and from about 6 to 8 in the colon. The polymeric material preferably has a pH threshold of about 6.5, i.e. is insoluble below pH 6.5 and soluble at about pH 6.5 or above, and more preferably has a pH threshold of about 7, i.e. is insoluble below pH 7 and soluble at about pH 7 or above.

The pH threshold at which a material becomes soluble may be determined by a simple titration technique which would be part of the common general knowledge to the person skilled in the art.

The polymer is typically a material such as a polymethacrylate polymer, a cellulose polymer or a polyvinyl-based polymer. Examples of suitable cellulose polymers include ethylcellulose, hydroxypropylcelullose, cellulose acetate phthalate (CAP); cellulose acetate trimellitate (CAT); and hydroxypropylmethylcellulose acetate succinate (HPMC-AS). Examples of suitable polyvinyl-based polymers include polyvinyl acetate phthalate (PVAP). Examples of suitable vinylpyrrolidone-vinyl acetate copolymers include Kollidon VA-64.

The polymer is preferably an "anionic" polymeric material, i.e. a polymeric material containing groups that are ionisable in aqueous media to form anions (see below), and more preferably a co-polymer of a (meth)acrylic acid and a (meth)acrylic acid $C_{1-4}$ alkyl ester, for example, a copolymer of methacrylic acid and methacrylic acid methyl ester. Such a polymer is known as a poly(methacrylic acid/methyl methacrylate) co-polymer. Suitable examples of such co-polymers are usually anionic and not sustained release polymethacrylates. The ratio of carboxylic acid groups to methyl ester groups (the "acid:ester ratio") in these co-polymers determines the pH at which the co-polymer is soluble. The acid:ester ratio may be from about 2:1 to about 1:3, e.g. about 1:1 or, preferably, about 1:2. The molecular weight ("MW") of preferred anionic co-polymers is usually from about 120,000 to 150,000 g/mol, preferably about 125,000 g/mol or about 135,000 g/mol.

Preferred anionic poly(methacrylic acid/methyl methacrylate) co-polymers have a molecular weight of about 125,000 g/mol. Suitable examples of such polymers have an acid:ester ratio of about 1:1 and a pH threshold of about pH 6, or have an acid:ester ratio of about 1:2 and a pH threshold of about pH 7.

A specific example of a suitable anionic poly(methacrylic acid/methyl methacrylate) co-polymer having a molecular weight of about 125,000 g/mol, an acid:ester ratio of about 1:1 and a pH threshold of about pH 6 is sold under the trade mark Eudragit® L. This polymer is available in the form of a powder (Eudragit® L 100), or as an organic solution (12.5%) (Eudragit® L 12.5).

A specific example of a suitable anionic poly(methacrylic acid/methyl methacrylate) co-polymer having a molecular weight of about 125,000 g/mol, an acid:ester ratio of about 1:2 and a pH threshold of about pH 7 is sold under the trade mark Eudragit® S. This polymer is available in the form of a powder (Eudragit® S 100) or as an organic solution (12.5%) (Eudragit® S 12.5).

The polymer may be a co-polymer of methacrylic acid and ethyl acrylate. Preferred poly(methacrylic acid/ethyl acrylate) co-polymers have a molecular weight from about 300,000 to 350,000 g/mol, e.g. about 320,000 g/mol. Suitable examples of such co-polymers have an acid:ester ratio of about 1:1 and a pH threshold of about pH 5.5.

A specific example of a suitable anionic poly(methacrylic acid/ethyl acrylate) co-polymer is available in the form of a powder and sold under the trade mark Eudragit® L 100-55, or in the form of an aqueous dispersion (30%) and sold under the trade mark Eudragit® L 30 D-55.

The polymeric material may be a co-polymer of methyl acrylate, methyl methacrylate and methacrylic acid. Preferred poly(methyl acrylate/methyl methacrylate/methacrylic acid) co-polymers have a molecular weight from about 250,000 to about 300,000 g/mol, e.g. about 280,000 g/mol. Suitable examples of such co-polymers have a methyl acrylate:methyl methacrylate:methacrylic acid ratio of about 7:3:1 thereby providing an acid:ester ratio of about 1:10 and a pH threshold of about pH 7.

A specific example of a suitable anionic poly(methyl acrylate/methyl methacrylate/ethyl acrylate) co-polymer is available in the form of an aqueous dispersion (30%) and is sold under the trade mark Eudragit® FS 30 D. Another specific example would be Eudragit® FS 100 which is the same as Eudragit® FS 30 D, but in powder form.

The Eudragit® co-polymers are manufactured and/or distributed by Evonik GmbH, Darmstadt, Germany.

Mixtures of polymers may be used as appropriate. For example, the polymeric material may be a blend of at least two different polymers having a pH threshold of about pH 5 and above.

Preferably, the polymers in the blend are different polymethacrylate polymers. In embodiments where the polymeric material is a blend of two different polymers having a pH threshold of about pH 5 or above, the polymers may be present in the blend in a polymer weight ratio from about 1:99 to about 99:1, .e.g. from about 10:90 to about 90:10, or from 25:75 to about 75:25, or from about 40:60 to about 60:40, for example about 50:50.

An example of a suitable mixture would include a mixture, e.g. a 1:1 mixture, of Eudragit® L and Eudragit® S. A further example would include a blend, e.g. a 50:50 blend, of Eudragit S and Eudragit FS.

For the avoidance of doubt, the terms "mixture" and "blend" in the context of mixtures or blends of polymers forming the polymeric material, are used herein interchangeably.

However, the use of a particular polymer material, e.g. a poly(methacrylic acid/methyl methacrylate) co-polymer, alone is preferred.

In a preferred embodiment applicable to all aspects of the invention, at least one polymer will be enteric, exhibiting pH-dependent-release and having a pH threshold in the range from 5.5 to 7, especially cellulosic enteric polymers.

Suitable particularly preferred polymers include hydroxypropylmethylcellulose acetate succinate (HPMC AS). Suitable polymers are available commercially, for instance, hypromellose acetate succinate (HPMC AS), AQOAT®, is available from Shin-Etsu Chemical Co. Ltd. Japan. This is marketed in three different grades depending on the ratio between acetyl and succinoyl groups—L, M and H—with pH thresholds of 5.5, 6.0 and 6.5 respectively.

In an alternative, equally preferred embodiment, also applicable to all aspects of the invention, the excipient comprises a polymeric material that dissolves in a pH-independent manner and which is rapid-disintegrating in the mouth or in aqueous media. Preferably the excipient further comprises a sugar and optionally a disintegrant. These excipients may be combined in appropriate weight percentages to provide immediate-release or orally-dissolving properties within the abilities of the skilled worker.

A specific example of a suitable polymeric material would be polyvinyl alcohol/polyethylene glycol graft copolymers (such as Kollicoat IR) or microcrystalline cellulose. Suitable sugars include mannitol, sorbitol and xylitol. Suitable disintegrants include crospovidone, crosslinked cellulose, crosslinked starch and the like.

In a preferred embodiment applicable to all aspects of the invention, at least one excipient is selected from the group consisting of methyl acrylate-methacrylic acid copolymers, ethyl acrylate-methacrylic acid copolymers, cellulose acetate succinate, hydroxy propyl methyl cellulose phthalate, hydroxypropylmethyl cellulose acetate succinate (hypromellose acetate succinate), polyvinyl acetate phthalate (PVAP), methyl methacrylate-methacrylic acid copolymers, Shellac, Cellulose acetate trimellitate, Sodium alginate, Zein, polyethylene oxide, ethylcellulose, hydroxypropyl cellulose, hydroxypropyl methylcellulose, polyvinylpyrrolidone, vinylpyrrolidone-vinyl acetate copolymers, gelatin, polysaccharides or mixtures thereof.

In all embodiments, applying to all aspects of the invention, the amount of excipient present is typically in the range of 15 wt. % to 99.5 wt. % by total weight of the mixture or formulation. For example, it may be preferable for the mixture to contain no more than 85 wt. % excipient, such as no more than 75 wt. %, no more than 60 wt. %, no more than 50 wt. %, no more than 40 wt. %, no more than 30 wt. % or no more than 20 wt. % excipient. It may be preferable for the mixture to contain no less than 70 wt. %, no less than 60 wt. %, no less than 50 wt. %, no less than 40 wt. %, no less than 30 wt. %, no less than 20 wt. %, no less than 10 wt. %, no less than 5 wt. % or no less than 1 wt. % of excipient, by total weight of the mixture or formulation.

Typical ranges of excipient content include, for example, 1-40 wt. %, such as 5-30 wt. % or 10-20 wt. %, and 50-80 wt. % such as 60-75 wt. % or 70-80 wt. %. Preferably the excipient comprises a polymer.

In one embodiment, applicable to all aspects of the invention, it is preferred to have 1 wt. % to 50 wt. % of at least one drug in combination with 20 wt. % to 80 wt. % of polymeric excipient, by total weight of the mixture or formulation.

In a preferred combination, applicable to all aspects of the invention, the mixture or formulation may comprise 1 wt. % to 15 wt. %, more preferably 3 wt. % to 10 wt. %, of at least one drug selected from the group of anti-inflammatory drugs, immunosuppressants, steroids, and antineoplastic drugs consisting of ibuprofen, diclofenac sodium, 5ASA (otherwise known as mesalazine or mesalamine), 4ASA, sulphasalazine, and balsalazide; azathioprine, cyclosporin, and methotrexate; prednisolone, budesonide and fluticasone; fluorouracil, methotrexate, dactinomycin, bleomycin, etoposide, taxol, vincristine, doxorubicin, cisplatin, daunorubicin, VP-16, raltitrexed, oxaliplatin; and pharmacologically acceptable derivatives and salts thereof; and 20 wt. % to 80 wt. %, more preferably 25 wt. % to 75 wt. %, of at least one polymeric excipient selected from the group consisting of methyl acrylate-methacrylic acid copolymers, ethyl acrylate-methacrylic acid copolymers, cellulose acetate succinate, hydroxy propyl methyl cellulose phthalate, hydroxypropylmethyl cellulose acetate succinate (hypromellose acetate succinate), polyvinyl acetate phthalate (PVAP), methyl methacrylate-methacrylic acid copolymers, Shellac, Cellulose acetate trimellitate, Sodium alginate, Zein, polyethylene oxide, ethylcellulose, hydroxypropyl cellulose, hydroxypropyl methylcellulose, polyvinylpyrrolidone, vinylpyrrolidone-vinyl acetate copolymers, gelatin and mixtures thereof.

In another preferred combination, applicable to all aspects of the invention, the mixture or formulation may comprise 1 wt. % to 15 wt. %, more preferably 3 wt. % to 10 wt. %, of at least one drug selected from the group of anti-inflammatory drugs, immunosuppressants, steroids, and antineoplastic drugs consisting of ibuprofen, diclofenac sodium, 5ASA (otherwise known as mesalazine or mesalamine), 4ASA, sulphasalazine, and balsalazide; azathioprine, cyclosporin, and methotrexate; prednisolone, budesonide and fluticasone; fluorouracil, methotrexate, dactinomycin, bleomycin, etoposide, taxol, vincristine, doxorubicin, cisplatin, daunorubicin, VP-16, raltitrexed, oxaliplatin; and pharmacologically acceptable derivatives and salts thereof; and 20 wt. % to 80 wt. %, more preferably 25 wt. % to 75 wt. %, of at least one polymeric excipient selected from the group consisting of polyvinyl alcohol/polyethylene glycol graft copolymers (such as Kollicoat IR) and microcrystalline cellulose; and 10-30 wt. %, more preferably 15-25 wt. % of a sugar such as mannitol, sorbitol or xylitol; and optionally a disintegrant such as include crospovidone, crosslinked cellulose, crosslinked starch and the like.

In a particularly preferred embodiment, applicable to all aspects of the invention, the mixture or formulation may comprise 3 wt. % to 10 wt. % of drug selected from ibuprofen, diclofenac sodium, 5ASA (otherwise known as mesalazine or mesalamine), 4ASA, sulphasalazine, and balsalazide; azathioprine, cyclosporin, and methotrexate; prednisolone, budesonide and fluticasone; fluorouracil, methotrexate, dactinomycin, bleomycin, etoposide, taxol, vincristine, doxorubicin, cisplatin, daunorubicin, VP-16, raltitrexed, oxaliplatin; and pharmacologically acceptable derivatives and salts thereof, and 20 wt. % to 80 wt. % of at least one cellulosic enteric polymer excipient such as hydroxypropylmethylcellulose acetate succinate.

In an embodiment preferred for "high" dose formulations, and applicable to all aspects of the invention, the mixture or formulation may comprise 65-85 wt. % of at least one drug, preferably selected from ibuprofen, diclofenac sodium, 5ASA (otherwise known as mesalazine or mesalamine), 4ASA, sulphasalazine, and balsalazide; azathioprine, cyclosporin, and methotrexate; prednisolone, budesonide and fluticasone; fluorouracil, methotrexate, dactinomycin, bleomycin, etoposide, taxol, vincristine, doxorubicin, cisplatin, daunorubicin, VP-16, raltitrexed, oxaliplatin; and pharmacologically acceptable derivatives and salts thereof; and 10 wt. % to 35 wt. % of at least one polymeric excipient selected from the group consisting of methyl acrylate-methacrylic acid copolymers, ethyl acrylate-methacrylic acid copolymers, cellulose acetate succinate, hydroxy propyl methyl cellulose phthalate, hydroxypropylmethyl cellulose acetate succinate (hypromellose acetate succinate), polyvinyl acetate phthalate (PVAP), methyl methacrylate-methacrylic acid copolymers, Shellac, Cellulose acetate trimellitate, Sodium alginate, Zein, polyethylene oxide, ethylcellulose, hydroxypropyl cellulose, hydroxypropyl methylcellulose, polyvinylpyrrolidone, vinylpyrrolidone-vinyl acetate copolymers, gelatin and mixtures thereof.

Preferably in this "high" dose formulation the polymeric excipient is selected from the group consisting of polyvinyl alcohol/polyethylene glycol graft copolymers (such as Kollicoat IR) and microcrystalline cellulose. The formulation may further comprise a sugar such as mannitol, sorbitol or xylitol, preferably 1-30 wt. %, more preferably 10-25 wt. % thereof; and optionally a disintegrant such as include crospovidone, crosslinked cellulose, crosslinked starch and the like.

The mixture may include two or more excipients, such as diluents or fillers, binders, disintegrants, colouring agents, preservatives, plasticizers, and lubricants.

Suitable fillers include mannitol, sorbitol, xylitol and sucrose. Suitable lubricants include magnesium stearate, silica and PEG.

A preferred feature of the excipient(s), applicable to all aspects and embodiments of the invention, is that the glass transition temperature of said excipient(s) is in the range from −100° C. to 250° C. Preferably at least one excipient in the mixture has a glass transition temperature in the range from −100° C. to 250° C.

Absorbent Materials

In an embodiment of the invention, applicable to all aspects of the invention, at least one of the drug or excipient absorbs electromagnetic radiation at a wavelength emitted by the laser.

In an alternative embodiment of the invention, applicable to all aspects of the invention, neither the drug nor the excipient absorbs electromagnetic radiation at a wavelength emitted by the laser and in this embodiment an absorbent material is required. The absorbent material is a material that absorbs electromagnetic radiation at a wavelength emitted by the laser.

For example, the absorbent material may absorb electromagnetic radiation having a wavelength in the range of from 200 nm to 11 μm, preferably 315 nm to 1.4 μm, more preferably 380 nm to 800 nm, such as 400 nm to 610 nm, preferably 400 nm to 500 nm, more preferably 430 nm to 470 nm In a preferred embodiment, applicable to all aspects of the invention, the absorbent material may absorb electromagnetic radiation having a wavelength in the range of from 10000 nm to 11000 nm, for example 10400-10800 nm, such as around 10600 nm.

In another equally preferred embodiment, equally applicable to all aspects of the invention, the absorbent material may absorb electromagnetic radiation having a wavelength in the range of from 700 nm to 900 nm, for example 750-850 nm, such as around 800 nm.

Suitable absorbent materials include inorganic absorbent materials, aromatic absorbent materials, azo compounds, natural colourants, dyes, pigments, and organic absorbent materials.

Examples of suitable inorganic absorbent materials include iron oxides, titanium oxides, titanium dioxide, silicates, and mixtures thereof, such as candurin.

Examples of suitable natural colourants include Cochineal insect, Cow urine, Lac insect, Murex snail, Octopus/Cuttlefish, Catechu or Cutch tree, Gamboge tree resin, Himalayan rubhada root, Indigofera plant, Kamala tree, Larkspur plant, Madder root, Myrabolan fruit, Pomegranate peel, and Weld herb, Examples of suitable aromatic absorbent materials include phthalocyanine and complexes of phthalocyanine.

Examples of suitable azo compounds include Acid orange 5, Acid orange 7, Acid red 88, Alcian yellow, Alizarine Yellow R, Allura Red AC, Amaranth (dye), Amido black 10B, Aniline Yellow, Arylide yellow, Azo violet, Azorubine, Biebrich scarlet, Bismarck brown Y, Black 7984, Brilliant Black BN, Brown FK, Brown HT, Chrysoine resorcinol, Citrus Red 2, Congo red, D&C Red 33, Diarylide pigment, Direct Blue 1, Disperse Orange 1, Eriochrome Black T, Evans Blue (dye), Fast Yellow AB, Hydroxynaphthol blue, Janus Green B, Lithol Rubine BK, Methyl orange, Methyl red, Methyl yellow, Mordant Brown 33, Mordant red 19, Oil Red O, Oil Yellow DE, Orange B, Orange G, Orange GGN, Para Red, Pigment Yellow 10, Ponceau 2R, Ponceau 4R, Ponceau 6R, Ponceau S, Prontosil, Red 2G, Scarlet GN, Solvent Red 26, Solvent Yellow 124, Sudan Black B, Sudan I, Sudan II, Sudan III, Sudan IV, Sudan Red 7B, Sudan Red G, Sudan stain, Sudan Yellow 3G, Sunset Yellow FCF, Tartrazine, Trypan blue, and Yellow 2G.

Examples of suitable dyes and pigments include phthalocyanine complexes, and carmine, also called cochineal, cochineal extract, crimson lake or carmine lake, natural red 4, C.I. 75470, or E120.

Examples of suitable organic absorbent materials include derivates of acridine, derivates of anthraquinone, Arylmethane dyes, Diarylmethane dyes based on diphenyl methane, derivates of triphenylmethane, Azo dyes based on —N=N— azo structure, Diazonium dyes based on diazonium salts, Nitro dyes based on a —NO2 nitro functional group, Nitroso dyes based on a —N=O nitroso functional group, derivatives of phthalocyanine, derivatives of quinone, Azin dyes, Eurhodin dyes, derivates of safranin, Indamins, derivates of indophenol, derivates of oxazin, derivates of oxazone, derivatives of thiazine, derivatives of thiazole, derivates of safranin, xanthene dyes, derivatives of fluorene, Pyronin dyes, Fluorone dyes, derivatives of rhodamine.

In a preferred embodiment applicable to all aspects of the invention, the absorbent material comprises iron oxide, titanium oxide, titanium dioxide, silicates, carmine, candurin, phtalocyanine, diazo compounds, or mixtures thereof.

Candurin (RTM) is a commercial product line provided by Merck Group. The current range of Candurin (RTM) materials includes:

CANDURIN®-SILVER COLORS
120600-Candurin® Silver Fine
120602-Candurin® Silver Lustre
120601-Candurin® Silver Sheen
120603-Candurin® Silver Sparkle
CANDURIN®-INTERFERENCE COLORS
120606-Candurin® Blue Shimmer
120604-Candurin® Gold Shimmer
120607-Candurin® Green Shimmer
120605-Candurin® Red Shimmer
CANDURIN®-GOLD COLORS
120610-Candurin® Gold Lustre
120608-Candurin® Gold Sheen
120623-Candurin® Gold Sparkle
120609-Candurin® Light Gold
CANDURIN®-IRON OXIDE COLORS
120622-Candurin® Red Sparkle
120617-Candurin® Brown Amber
120615-Candurin® Orange Amber
120613-Candurin® Red Amber
120619-Candurin® Red Lustre Typical ranges of content for the absorbent materials include, for example, 0.1-50 wt. %, such as 0.1-30 wt. %, 5-25 wt. % or 10-20 wt. %.

In one embodiment, applicable to all aspects of the invention, it is preferred to have 1 wt. % to 50 wt. % of at least one drug in combination with 5 wt. % to 80 wt. % of excipient, and 0.1-30 wt. % of absorbent material, by total weight of the mixture or formulation.

In a preferred combination, applicable to all aspects of the invention, the mixture or formulation may comprise 1 wt. % to 15 wt. %, more preferably 3 wt. % to 10 wt. %, of at least one drug selected from the group of anti-inflammatory drugs, immunosuppressants, steroids, and antineoplastic drugs consisting of ibuprofen, diclofenac sodium, 5ASA (otherwise known as mesalazine or mesalamine), 4ASA, sulphasalazine, and balsalazide; azathioprine, cyclosporin, and methotrexate; prednisolone, budesonide and fluticasone; fluorouracil, methotrexate, dactinomycin, bleomycin, etoposide, taxol, vincristine, doxorubicin, cisplatin, daunorubicin, VP-16, raltitrexed, oxaliplatin; and pharmacologically acceptable derivatives and salts thereof; and 20 wt. % to 80 wt. %, more preferably 25 wt. % to 75 wt. %, of at least one polymeric excipient selected from the group consisting of methyl acrylate-methacrylic acid copolymers, ethyl acrylate-methacrylic acid copolymers, cellulose acetate succinate, hydroxy propyl methyl cellulose phthalate, hydroxypropylmethyl cellulose acetate succinate (hypromellose acetate succinate), polyvinyl acetate phthalate (PVAP), methyl methacrylate-methacrylic acid copolymers, Shellac, Cellulose acetate trimellitate, Sodium alginate, Zein, polyethylene oxide, ethylcellulose, hydroxypropyl cellulose, hydroxypropyl methylcellulose, polyvinylpyrrolidone, vinylpyrrolidone-vinyl acetate copolymers, gelatin and mixtures thereof; and 0.1-30 wt. %, more preferably 5-20 wt. % of at least one absorbent material comprising iron oxide, titanium oxide, titanium dioxide, silicates, carmine, candurin, phtalocyanine, diazo compounds, or mixtures thereof.

In a particularly preferred embodiment, applicable to all aspects of the invention, the mixture or formulation may comprise 3 wt. % to 10 wt. % of drug selected from ibuprofen, diclofenac sodium, 5ASA (otherwise known as mesalazine or mesalamine), 4ASA, sulphasalazine, and balsalazide; azathioprine, cyclosporin, and methotrexate; prednisolone, budesonide and fluticasone; fluorouracil, methotrexate, dactinomycin, bleomycin, etoposide, taxol, vincristine, doxorubicin, cisplatin, daunorubicin, VP-16, raltitrexed, oxaliplatin; and pharmacologically acceptable derivatives and salts thereof; 20 wt. % to 80 wt. % of at least one cellulosic enteric polymer excipient such as hydroxypropylmethylcellulose acetate succinate; and 5-15 wt. % of at least one absorbent material comprising iron oxide, titanium oxide, titanium dioxide, silicates, carmine, candurin, phthalocyanine or mixtures thereof.

In an embodiment preferred for "high" dose formulations, and applicable to all aspects of the invention, the mixture or formulation may comprise 65-85 wt. % of at least one drug, preferably selected from ibuprofen, diclofenac sodium, 5ASA (otherwise known as mesalazine or mesalamine), 4ASA, sulphasalazine, and balsalazide; azathioprine, cyclosporin, and methotrexate; prednisolone, budesonide and fluticasone; fluorouracil, methotrexate, dactinomycin, bleomycin, etoposide, taxol, vincristine, doxorubicin, cisplatin, daunorubicin, VP-16, raltitrexed, oxaliplatin; and pharmacologically acceptable derivatives and salts thereof; 10 wt. % to 35 wt. % of at least one polymeric excipient selected from the group consisting of methyl acrylate-methacrylic acid copolymers, ethyl acrylate-methacrylic acid copolymers, cellulose acetate succinate, hydroxy propyl methyl cellulose phthalate, hydroxypropylmethyl cellulose acetate succinate (hypromellose acetate succinate), polyvinyl acetate phthalate (PVAP), methyl methacrylate-methacrylic acid copolymers, Shellac, Cellulose acetate trimellitate, Sodium alginate, Zein, polyethylene oxide, eth- ylcellulose, hydroxypropyl cellulose, hydroxypropyl methylcellulose, polyvinylpyrrolidone, vinylpyrrolidone-vinyl acetate copolymers, gelatin and mixtures thereof; and 1-15 wt. % of at least one absorbent material comprising iron oxide, titanium oxide, titanium dioxide, silicates, carmine, candurin, phthalocyanine or mixtures thereof.

Preferably in this "high" dose formulation the polymeric excipient is selected from the group consisting of polyvinyl alcohol/polyethylene glycol graft copolymers (such as Kollicoat IR) and microcrystalline cellulose. The formulation may further comprise a sugar such as mannitol, sorbitol or xylitol, preferably 1-30 wt. %, more preferably 10-25 wt. % thereof; and optionally a disintegrant such as include crospovidone, crosslinked cellulose, crosslinked starch and the like.

Mixtures

Preferably the mixture of drug(s) and excipient(s) will be a heterogeneous mixture. A heterogeneous mixture is defined in the art as a mixture that is composed of components that are not uniform, or has localised regions that have different properties. In the current invention the mixture is preferably heterogeneous in the sense that the drug(s) and excipient(s) have different melting points.

Preferably the mixture is ground before undergoing printing, preferably to a particle size of less than 500 microns (µm). For example, 1-100 microns, preferably 10-50 microns.

Preferred Mixtures In a preferred embodiment, applicable to all aspects of the invention, the mixture comprises:
(a) 2 wt. % to 10 wt. % of at least one drug selected from ibuprofen, diclofenac sodium, 5ASA (otherwise known as mesalazine or mesalamine), 4ASA, sulphasalazine, and balsalazide; azathioprine, cyclosporin, and methotrexate; prednisolone, budesonide and fluticasone; fluorouracil, methotrexate, dactinomycin, bleomycin, etoposide, taxol, vincristine, doxorubicin, cisplatin, daunorubicin, VP-16, raltitrexed, oxaliplatin; and pharmacologically acceptable derivatives and salts thereof;
(b) 20 wt. % to 80 wt. % of at least one cellulosic enteric polymer such as hydroxypropylmethylcellulose acetate succinate;
(c) 0.5 wt. % to 10 wt. % of at least one of iron oxide, titanium oxide, silicates, candurin, carmine or mixtures thereof.

In another equally preferred embodiment applicable to all aspects of the invention the mixture includes:
(a) 3 wt. % to 10 wt. % of at least one drug selected from ibuprofen, diclofenac sodium, 5ASA (otherwise known as mesalazine or mesalamine), 4ASA, sulphasalazine, and balsalazide; azathioprine, cyclosporin, and methotrexate; prednisolone, budesonide and fluticasone; fluorouracil, methotrexate, dactinomycin, bleomycin, etoposide, taxol, vincristine, doxorubicin, cisplatin, daunorubicin, VP-16, raltitrexed, oxaliplatin; and pharmacologically acceptable derivatives and salts thereof;
(b) 20 wt. % to 80 wt. % of at least one of Kollicoat IR and polyethylene oxide;
(c) 0.5 wt. % to 10 wt. % of at least one of iron oxide, titanium oxide, silicates, candurin, carmine or mixtures thereof.

In another preferred combination, applicable to all aspects of the invention, the mixture includes:
(a) 1 wt. % to 15 wt. %, more preferably 3 wt. % to 10 wt. %, of at least one drug;
(b) 20 wt. % to 80 wt. %, more preferably 25 wt. % to 75 wt. %, of at least one polymeric excipient selected from the group consisting of polyvinyl alcohol/polyethylene glycol graft copolymers (such as Kollicoat IR) and microcrystalline cellulose;
(c) 10-30 wt. %, more preferably 15-25 wt. % of a sugar such as mannitol, sorbitol or xylitol;
(d) optionally a disintegrant such as include crospovidone, crosslinked cellulose, crosslinked starch and the like;
(e) 0.5 wt. % to 10 wt. % of at least one of iron oxide, titanium oxide, silicates, candurin, carmine or mixtures thereof.

In another preferred combination, applicable to all aspects of the invention, the mixture includes:
(a) 1 wt. % to 15 wt. %, more preferably 3 wt. % to 10 wt. %, of at least one drug selected from ibuprofen, diclofenac sodium, 5ASA (otherwise known as mesalazine or mesalamine), 4ASA, sulphasalazine, and balsalazide; azathioprine, cyclosporin, and methotrexate; prednisolone, budesonide and fluticasone; fluorouracil, methotrexate, dactinomycin, bleomycin, etoposide, taxol, vincristine, doxorubicin, cisplatin, daunorubicin, VP-16, raltitrexed, oxaliplatin; and pharmacologically acceptable derivatives and salts thereof;
(b) 50 wt. % to 98.5 wt. %, more preferably 80 wt. % to 95 wt. %, of at least one polymeric excipient selected from the group consisting of vinylpyrrolidone-vinyl acetate copolymers (such as Kollidon VA-64), polyvinyl alcohol/polyethylene glycol graft copolymers (such as Kollicoat IR) and microcrystalline cellulose;
(c) 0.5 wt. % to 10 wt. %, more preferably 1 wt. % to 5 wt. % of at least one of iron oxide, titanium oxide, silicates, candurin, carmine or mixtures thereof.

In an embodiment preferred for "high" dose formulations, and applicable to all aspects of the invention, the mixture or formulation includes:
(a) 65 wt. % to 85 wt. % of at least one drug selected from ibuprofen, diclofenac sodium, 5ASA (otherwise known as mesalazine or mesalamine), 4ASA, sulphasalazine, and balsalazide; azathioprine, cyclosporin, and methotrexate; prednisolone, budesonide and fluticasone; fluorouracil, methotrexate, dactinomycin, bleomycin, etoposide, taxol, vincristine, doxorubicin, cisplatin, daunorubicin, VP-16, raltitrexed, oxaliplatin; and pharmacologically acceptable derivatives and salts thereof;
(b) 10 wt. % to 35 wt. % of at least one polymeric excipient selected from the group consisting of methyl acrylate-methacrylic acid copolymers, ethyl acrylate-methacrylic acid copolymers, cellulose acetate succinate, hydroxy propyl methyl cellulose phthalate, hydroxypropylmethyl cellulose acetate succinate (hypromellose acetate succinate), polyvinyl acetate phthalate (PVAP), methyl methacrylate-methacrylic acid copolymers, Shellac, Cellulose acetate trimellitate, Sodium alginate, Zein, polyethylene oxide, ethylcellulose, hydroxypropyl cellulose, hydroxypropyl methylcellulose, polyvinylpyrrolidone, vinylpyrrolidone-vinyl acetate copolymers, gelatin and mixtures thereof;
(c) 1 wt. % to 15 wt. % of at least one of iron oxide, titanium oxide, titanium dioxide, silicates, carmine, candurin, phthalocyanine or mixtures thereof.

Preferably in this "high" dose formulation the polymeric excipient is selected from the group consisting of polyvinyl alcohol/polyethylene glycol graft copolymers (such as Kollicoat IR) and microcrystalline cellulose. The formulation may further comprise a sugar such as mannitol, sorbitol or xylitol, preferably 1-30 wt. %, more preferably 10-25 wt. % thereof; and optionally a disintegrant such as include crospovidone, crosslinked cellulose, crosslinked starch and the like.

In another preferred embodiment applicable to all aspects of the invention, suitable mixtures may comprise 3 wt. % to 10 wt. %, such as about 5 wt. %, of at least one drug selected from ibuprofen, diclofenac sodium, 5ASA (otherwise known as mesalazine or mesalamine), 4ASA, sulphasalazine, and balsalazide; azathioprine, cyclosporin, and methotrexate; prednisolone, budesonide and fluticasone; fluorouracil, methotrexate, dactinomycin, bleomycin, etoposide, taxol, vincristine, doxorubicin, cisplatin, daunorubicin, VP-16, raltitrexed, oxaliplatin; and pharmacologically acceptable derivatives and salts thereof, with the other excipients as listed in table 1.

TABLE 1 exemplary preferred mixtures (% by total weight of mixture, including drug)

| Excipient | % Absorbent material (Gold Colourant) |
|---|---|
| PVA 87-89% HYDROLISED (MW 13-23 Kda) | 3 |
| PVA 87-90% HYDR. (MW 30-70 Kda) | 3 |
| PVA NIPPON GOHSEI | 3 |
| KOLLICOAT IR (PEG 25% + PVA 75%) | 3 |
| KOLLICOAT PROTECT (KOLLICOAT IR + PVA) | 3 |
| PVA 87-89% HYDROLISED (MW 13-23 Kda) + MANNITOL (50/50) | 3 |
| PVA 87-89% HYDROLISED (MW 13-23 Kda) + MANNITOL (35/65) | 3 |
| PVA NIPPON + PEO 7M (80/20) | 4 |
| KOLLICOAT IR + MANNITOL (80 + 20) | 3 |
| KOLLICOAT IR + MANNITOL (60 + 40) | 3 |
| KOLLICOAT IR + MANNITOL SIGMA (80/20) | 3 |
| KOLLICOAT IR + MANNITOL SIGMA (60/40) | 3 |
| EUDRAGIT L100-55 | 3 |
| EUDRAGIT RS PO | 3 |
| EUDRAGIT RL PO | 3 |
| EUDRAGIT FS100 | 3 |
| EUDRAGIT S100 | 10 |
| EUDRAGIT L100 | 5 |
| EUDRAGIT L100-55 + PEO 600 Kda (70/30) | 3 |
| EUDRAGIT L100-55 + PEO 7M (90/10) | 5 |
| EUDRAGIT L100-55 + PEO 7M (95/5) | 5 |

TABLE 1-continued exemplary preferred mixtures (% by total weight of mixture, including drug)

| Excipient | % Absorbent material (Gold Colourant) |
|---|---|
| EUDRAGIT L100-55 + PEO 7M (90/10) | 5 |
| EUDRAGIT L100-55 + PEO 7M (90/10) | 5 |
| EUDRAGIT L100-55 + PEO 7M (80/20) | 5 |
| EUDRAGIT L100-55 + PEO 7M (90/10) DOUBLE LAYER | 5 |
| HPMC ASHLAND BENECEL K100LV PH PRM | 3 |
| HPMC ASHLAND BENECEL K4M PHARM CR | 3 |
| MC BENECEL A15LV PH PRM | 3 |
| HEC HERCULES NATROSOL Pharm 250M PHARM | 3 |
| HPC KLUCEL ASHLAND LF PHARM | 6 |
| HPC KLUCEL ASHLAND EF PHARM | 3 |
| HPC KLUCEL ASHLAND MF PHARM | 3 |
| HPC KLUCEL ASHLAND GF PHARM | 6 |
| CELLULOSE ACETATE ALDRICH 39.8% ACETYL CONTENT MW 30000 | 3 |
| ETHYLCELLULOSE DOW | 3 |
| ETHYLCELLULOSE ALDRICH 46 Cp | 3 |
| ETHYLCELLULOSE (AQUALON EC-N7) | 3 |
| ETHYLCELLULOSE ACROSS CP 10 | 3 |
| ETHYLCELLULOSE ACROSS 10 cps + PEO 7M (90/10) | 3 |
| AQOAT AS-LG SHIN ETSU | 3 |
| AQOAT AS-MG SHIN ETSU | 3 |
| AQOAT AS-HG SHIN ETSU | 3 |
| AQOAT AS-MG + PEO 7M (90/10) | 3 |
| POLYOX 100 Kda | 3 |
| POLYOX N-12 K | 3 |
| PEO 8M SIGMA | 3 |
| PEO 300 KDa + SHELLAC SSB 55 (50/50) | 1.5 |
| PEO 300 KDa + KOLLIPHOR P188 (50/50) | 3 |
| PEO 300 KDa + EUDRAGIT RS PO (50/50) | 3 |
| SHELLAC WAX-FREE SIGMA | None |
| SHELLAC SSB 55 | None |
| SHELLAC SSB 55 + PVA NIPPON (60/40) | None |
| SHELLAC SSB 55 + PVA NIPPON (50/50) | None |
| SHELLAC SSB 55 + KOLLICOAT IR (50/50) | 1.5 |
| SHELLAC SSB 55 + XANTHAN GUM (50/50) | None |
| SHELLAC SSB 55 + EUDRAGIT RS PO (50/50) | 1 |
| SHELLAC SSB 55 + MANNITOL (70/30) | None |
| PVP 40000 MW SIGMA | 3 |
| PVP 10000 MW SIGMA | 3 |
| PVP360000 MW SIGMA | 3 |
| PVP SIGMA 360 KDa + PEO 7M (90/10) | 3 |
| KOLLIDON VA-64 | 3 |

Absorption of Electromagnetic Radiation

In one embodiment, applicable to all aspects of the invention, the mixture comprises a drug and an excipient and at least one of the drug or excipient absorbs electromagnetic radiation at a wavelength emitted by the laser.

Either or both of the drug and excipient can absorb electromagnetic radiation at a wavelength emitted by the laser. Preferably, the excipient absorbs electromagnetic radiation at a wavelength emitted by the laser.

In another embodiment, equally applicable to all aspects of the invention, the mixture comprises a drug, an excipient and an absorbent material which absorbs electromagnetic radiation at a wavelength emitted by the laser.

The mixture must include a material that absorbs electromagnetic radiation at a wavelength emitted by the laser in order for the process to take place without degradation of the drug. This can be achieved by having a drug and/or excipient which absorbs in the appropriate region, and/or by using an absorbent material which absorbs in the appropriate region.

Absorption is defined as the way in which the energy of a photon is taken up by matter. Thus, the electromagnetic energy is transformed into internal energy of the absorbent material, for example thermal energy.

There are a number of ways to quantify how quickly and effectively radiation is absorbed in a certain medium, for example by means of the absorption coefficient, and some closely related derived quantities such as:

The attenuation coefficient, which is sometimes but not always synonymous with the absorption coefficient;

Molar absorptivity, also called "molar extinction coefficient", which is the absorption coefficient divided by molarity;

The mass attenuation coefficient, also called "mass extinction coefficient", which is the absorption coefficient divided by density.

All these quantities measure, at least to some extent, how well a medium absorbs radiation. The absorbance of an object quantifies how much of the incident radiation, for example light, is absorbed by it (instead of being reflected or refracted). This may be related to other properties of the object by the skilled worker in the art, for example using the Beer-Lambert law.

Precise measurements of the absorbance at many wavelengths allow the identification of a substance via absorption spectroscopy, where a sample is illuminated from one side and the intensity of the radiation, for example light, that exits from the sample in every direction is measured. Examples of absorption techniques include ultraviolet-visible spectroscopy, infrared spectroscopy, and X-ray absorption spectroscopy.

In the context of the current invention, the absorption of electromagnetic radiation is quantified in terms of the molar absorptivity. This can be measured and/or calculated using standard methods in the art, commonly absorption/transmission/reflectance spectroscopy. This technique can measure absorption over a range of wavelengths and it would be a routine matter for the skilled worker in the art to establish whether a particular drug, excipient or absorbent material will absorb at a particular wavelength, using this technique.

Preferably the drug and/or excipient and/or absorbent material which absorbs electromagnetic radiation at a wavelength emitted by the laser has an absorbance of at least 0.01 at that wavelength, as measured by spectroscopy under the specific conditions. Suitable equipment will be known to the skilled worker in the art. For example, UV-Vis-NIR spectrophotometers are available from manufacturers including Shimadzo (e.g. UV-2600, UV-2700). Absorbance, such as at wavelengths between 200-1400 nm, can be measured by UV-Vis-NIR spectroscopy at room temperature (approximately 25° C.) using a reflecting chamber. "Diffuse Reflectance Accessory(DRA)". Typically 0.15 g of material to be evaluated (e.g. polymers or mixture of polymer and drug) is blended with 0.5 g of barium sulphate that is compressed and introduced in the spectrophotometer. For example Agilent Cary equipment (e.g. Cary 4000) can be used to determine UV-visible-infrared spectra characteristics of powders over wavelengths from 290-1000 nm, without dissolving in solvents such as methanol, by using a Diffuse Reflectance or Praying Mantis Accessories.

It is preferred, in all aspects and embodiments of the invention, that the drug has a molar absorptivity of less than $1000$ L mol$^{-1}$ cm$^{-1}$ at wavelengths between 290-700 nm, as measured by UV-Vis spectroscopy at room temperature (approximately 25° C.). In other words, it is preferred that the drug is not photoreactive or is not photoreactive to a degree resulting in potential photosafety concerns. Typically, for most drugs, useful UV-Vis spectra can be obtained at concentrations around 100 microns, in a methanol solvent.

For all embodiments and aspects of the invention where the drug is to be delivered transdermally it is preferred for the excipient(s) also to have a molar absorptivity of less than $1000$ L mol$^{-1}$ cm$^{-1}$ at wavelengths between 290-700 nm, as measured by UV-Vis spectroscopy at room temperature (approximately 25° C.), typically using a methanol solvent.

Powder Bed Fusion Selective Laser 3-Dimensional Printing 3-dimensional printing generally relates to processes used for manufacturing solid objects of almost any shape starting from computer aided design (CAD) files and based on the addition of materials layer by layer (additive manufacturing). Each layer represents a cross-section of the object derived from the virtual model and is in turn printed on the previous one so that the final product will constitute an approximation of that model, the resolution of which increases with the reduction of the layer thickness. The process occurs automatically, under computer control, in principle avoiding any Manual task (automated fabrication), and the time and costs of manufacturing do not depend on the complexity of the product geometry.

Generally, Powder Bed Fusion (PBF) 3DP methods use either a laser or electron beam to melt or fuse material powder together. Electron beam melting (EBM) methods require a vacuum but are typically used with metals and alloys in the creation of functional parts. PBF laser methods are used in the current invention.

All PBF processes involve the spreading of the powder material over previous layers. There are different mechanisms to enable this, including, for example, a roller or a blade. A hopper or reservoir below or beside the bed provides a supply of fresh material.

In PBF Selective Laser methods, thin layers of powder are distributed and then selectively joined by laser radiations used to sinter or melt (fully or partially) the layered powders. The process sinters/melts the powder, layer by layer.

A typical PBF Selective Laser 3DP process includes the following steps:

(i) a layer, typically 0.1 mm thick, of material is spread over the build platform;

(ii) a laser fuses the first layer or first cross-section of the model;

(iii) a new layer of powder is spread across the previous layer using a roller;

(iv) further layers or cross sections are fused and added;

The process repeats until the entire model is created. Loose, unfused powder is remains in position but is removed during post-processing. FIG. 1 shows a typical PBF Selective Laser 3DP process.

Typical PBF Selective Laser 3DP methods include Selective Laser Sintering and Selective Laser Melting. These methods are similar, differing in the temperatures applied by the laser at the printing surface (surface temperature) and the resultant degree of melting of the powder material that is achieved during the process. In Selective Laser Sintering, the powder particles are fused or agglomerated by sintering, without liquification. In Selective Laser Melting there is full or partial liquification of the powder particles. Otherwise, features and parameters which are described with respect only to selective laser sintering are also applicable in respect of selective laser melting.

Selective Laser Sintering 3DP, Selective Laser Melting 3DP, and mixtures thereof, are equally suitable for the process of the current invention. In a preferred embodiment, applicable to all aspects of the invention, the powder bed fusion selective laser 3DP process comprises selective laser sintering 3DP.

Selective Laser Sintering (SLS) 3-Dimensional Printing

SLS 3DP involves the distribution of thin layers of powder selectively joined by laser radiations used to fuse or agglomerate the layered powders. A suitable SLS machine typically preheats the bulk powder material in the powder bed to a temperature close to but below its melting point, to make it easier for the laser to raise the temperature of the selected regions the rest of the way to the working temperature.

SLS 3DP is typically used in printing plastic, ceramic or metals. The sintered materials form part of the final object while the unsintered materials remain as part of the supporting structure.

SLS 3DP has been utilized in medical applications in areas such as manufacture of bespoke implants or fabrication of scaffolds in tissue engineering. However, to date, it has not been used in pharmaceutical applications because it was believed that the high energy input from the laser beam would degrade the drug and/or excipients. In fact it was predicted in the art that SLS technology is unlikely to be adaptable to successfully print drug formulations (due to degradation of polymers or drugs).

FIG. 2 shows a schematic of a typical SLS 3D printer.

Suitable printers for SLS 3DP according to the invention include, for example, machines manufactured by EOS GmbH (Germany), such as FORMICA® P 110, EOSINT® P 395, EOSINT® P 760, and EOSINT® P 800 equipment. Suitable SLS 3D printing machines manufactured by 3D Systems Inc. are exemplified by their SPRO® line of equipment. Other suitable printers include those manufactured by Sintratec, Sinterit and Sinterstation, for example the DTM Sinterstation 2500 RP system.

Parameters that can be varied in SLS 3DP typically include the type of laser and thus its wavelength, as well as the laser power, scan speed, print resolution (layer height), beam spot size, surface temperature, chamber temperature, and the initial position of the build platform and its lowering speed.

A laser is a device that emits light through a process of optical amplification based on the stimulated emission of electromagnetic radiation. The term "laser" originated as an acronym for "light amplification by stimulated emission of radiation". Lasers emit light coherently.

Types of lasers used in SLS 3DP include, for example, CO2 lasers, infrared lasers, and diode lasers such as blue diode lasers.

The wavelength of electromagnetic radiation emitted by lasers suitable for SLS 3DP is typically within the range of 200 nm to 11 microns. In other words typically in the near ultra-violet through to the mid-infrared part of the electromagnetic spectrum. For example, suitable lasers may emit electromagnetic radiation in the range of 315 nm to 1.4 microns, such as 400-610 nm, preferably 400-500 nm, more preferably 430-470 nm. Another suitable laser emits electromagnetic radiation in the range of 9.4 to 11 microns, such as 10.2-10.8 microns, preferably around 10.6 microns. Another suitable laser emits electromagnetic radiation in the range of 750-850 nm, such as approximately 800 nm.

The power of a laser is measured in Watts. This is referring to the optical power output of the laser beam, which is the continuous power output of continuous wave (CVV) lasers, or the average power of a pulsed or modulated laser. Typically, SLS 3D printers use continuous wave lasers.

Lasers suitable for SLS 3DP according to this invention typically have a power in the range of 0.5 W to 140 W. In all aspects and embodiments of this invention it is preferred if the laser has a power in the range of at least 1 W to less than 80 W, for example, 1.5-75 W. More preferably the laser power may be in the range of 1.7-8 W, such as 1.8-5 W, for example 2-3 W.

Suitable SLS 3D printers may use more than one laser. For example, printers may use two lasers, or more than two lasers. For example, a suitable printer may use two lasers each having a power in the range of 1.5-75 W, for example two lasers of around 65-75 W power, such as around 70 W power.

The scan speed for SLS 3DP is the rate at which the laser moves over the powder bed. Suitable scan speeds for the current invention range from about 5 mm/s to about 50000 mm/s. For example, the scan speed may be in the range from 10-1000 mm/s or 1270-12700 mm/s. The scan speed correlates directly with the laser beam interaction time. A slower scan speed results in a longer laser beam interaction time.

In a preferred embodiment, applicable to all aspects of the invention, the scan speed may be in the range from 10 mm/s to 1000 mm/s, preferably 20-300 mm/s, more preferably from 30-200 mm/s, e.g. 90 mm/s.

According to the present invention it is preferred to use a layer height in the range of 0.001 mm to 10 mm, preferably 0.025 mm to 0.5 mm, more preferably 0.05 to 0.25 mm, such as 0.1 mm. It is believed that reduction in the layer thickness provides better i.e. increased print resolution of the object printed.

Suitable beam spot size for the present invention is typically in the range of from 0.0025 mm to 1 mm, for example 0.05-0.5 mm, preferably 0.1-0.3 mm, for example 0.2 mm. Increasing the spot size can be used to increase the laser beam interaction time. Typically, this is influenced by adjusting the scan speed, however.

The surface temperature is the temperature of the powder that is being sintered. Typically the surface temperature will be in the range of 0-200° C., preferably 40-180° C., most preferably 70-170° C.

The chamber temperature is the temperature within the chamber in which printing is taking place. Typically this is in the range of 25-200° C., preferably 60-150° C.

TABLE 2 exemplary preferred combinations of printing parameters
PRINTING PARAMETERS

| Chamber Temp in ° C. | Surface Temp in ° C. | Laser scan speed in mm/sec |
|---|---|---|
| 170 | 150 | 110 |
| 170 | 150 | 70 |
| 130 | 95 | 60 |
| 120 | 90 | 90 |
| 160 | 140 | 110 |
| 150 | 130 | 110 |
| 135 | 120 | 64 |
| 120 | 94 | 100 |
| 130 | 120 | 150 |
| 130 | 100 | 70 |
| 130 | 100 | 200 |
| 120 | 80 | 80 |
| 65 | 54 | 70 |
| 65 | 52 | 100 |
| 130 | 100 | 55 |
| 130 | 100 | 60 |
| 85 | 60 | 45 |
| 90 | 60 | 40 |
| 140 | 115 | 60 |
| 140 | 115 | 60-75 |
| 135 | 115 | 70 |
| 140 | 160 | 100 |
| 140 | 166 | 100 |
| 140 | 166 | 101 |
| 100 | 125 | 80 |
| 100 | 130 | 75 |
| 100 | 130 | 35 |
| 100 | 135 | 38 |
| 120 | 100 | 100 |
| 130 | 105 | 85 |
| 130 | 109 | 50 |
| 130 | 100 | 93 |
| 130 | 100 | 70 |
| 125 | 105 | 90 |
| 130 | 100 | 90 |
| 125 | 105 | 120 |
| 55 | 35 | 100 |
| 55 | 33 | 35-70 |
| 60 | 40 | 35 |
| 70 | 55 | 30 |
| 50 | 36 | 150 |
| 65 | 50 | 35-70 |
| 60 | 50 | 125 |
| 60 | 50 | 50 |
| 55 | 40 | 40 |
| 62 | 54 | 18 |
| 60 | 40 | 20 |
| 70 | 50 | 29 |
| 70 | 60 | 60 |
| 75 | 60 | 19 |
| 150 | 120 | 50 |
| 150 | 120 | 130 |
| 160 | 150 | 70 |
| 80 | 100 | 100 |
| 90 | 110 | 90 |
| 35 | 50 | 200 |
| 35 | 50 | 300 |
| 35 | 50 | 400 |

Without being bound by theory it is believed that the combination of scan speed and laser power may affect the drug release properties in the formulations. For example, the combination of a high power laser with a high scan speed can provide the same release properties as the combination of low power laser with a low scan speed. This is believed to be due to the influence of these two parameters on the power transferred from the laser into the powder being sintered. A long laser beam interaction time, which is directly related to scan speed, e.g. with a slow scan speed, in combination with a low power laser, provides a certain energy input into the powder. The same energy input into the powder could be achieved using a shorter laser beam interaction time, i.e. faster scan speed, if the laser power is higher.

The Andrew number (AN) measures the energy density delivered to the image plane (effective energy exposure of the dosage form).

Andrew number is defined as:

$$A_N = \frac{P}{V \cdot HS}$$

where P=laser power in W, V=scan speed in m/s and HS=hatch spacing in m.

It is evident from the above equation that the same Andrew number can be achieved using different combinations of scan speed and power.

In SLS 3DP the particles of powder are fused together or agglomerated by sintering. Sintering is the process of compacting and forming a solid mass of material by heat or pressure without melting it to the point of liquefaction. Sintering happens naturally in mineral deposits or as a general manufacturing process used with metals, ceramics, plastics, and other materials. The atoms in the materials diffuse across the boundaries of the particles, fusing the particles together and creating one solid piece. Because the sintering temperature does not have to reach the melting point of the material, sintering is often chosen as the shaping process for materials with extremely high melting points such as tungsten and molybdenum.

Sintering is typically used to reduce the porosity of a material and enhance properties such as strength, electrical conductivity, translucency and thermal conductivity. In other cases, it may be useful to increase the material strength but keep its gas absorbency constant as in filters or catalysts. During the firing process, atomic diffusion drives powder surface elimination in different stages, starting from the formation of necks between powders to final elimination of small pores at the end of the process.

SLS 3-dimensional printers can provide dosage forms having a range of geometries. For example, cylindrical, prismatic, oval, elongated, capsule-shaped, diamond-shaped, lattice structures, thin films. This is typically controlled by the CAD software. Typical geometries are shown in FIG. 3.

The use of high processing temperatures (>168° C.) and an inert nitrogen environment in the SLS process chamber may ensure that the parts are fabricated within a sterile environment.

Selective Laser Melting (SLM) 3-Dimensional Printing SLM 3DP involves the distribution of thin layers of powder selectively joined by laser radiations used to melt (fully or partially) the layered powders. A suitable SLM machine typically preheats the bulk powder material in the powder bed to a temperature close to but below its melting point, to make it easier for the laser to raise the temperature of the selected regions the rest of the way to the melting point.

Suitable SLS 3D printers are typically also suitable for SLM 3DP, and the same parameters described above can be varied for SLM processes according to the invention.

Solid pharmaceutical dosage formulations

The term "pharmaceutical dosage formulation" means a dosage form or unit dose, such as an ODT, or a tablet or caplet, containing a drug. It is not intended that this term includes drug delivery devices that are surgically inserted, such as implants.

Typically the dosage forms may be cylindrical, spherical, prismatic, oval, capsule-shape, or elongate, or diamond shaped. The solid pharmaceutical dosage formulations may be prepared with a variety of physical forms, including tablets, caplets, orally-disintegrating tablets, films, masks and patches.

The solid pharmaceutical dosage formulations may be prepared with a range of release-behaviour. The solid pharmaceutical dosage forms according to the invention may provide at least one of modified release, immediate release, colonic delivery, enteric delivery, or gastroretentive drug delivery performance.

Preferably, controlled-release is provided, specifically enteric-release that is pH-dependent, for example having a pH-threshold of at least 5, for example 5.5-7.

Alternatively, and equally preferably, immediate release is provided, preferably via orally-disintegrating tablet (ODT).

The solid dosage pharmaceutical formulations, may be suitable for administration via oral, buccal, topical, transdermal, sublingual, enteral, dental, rectal, urethral or vaginal routes. Preferably oral, buccal, topical or transdermal administration may be used. Oral administration can include buccal, oral-mucosal administration, sublabial and sublingual administration but the current invention preferably relates to oral administration by swallowing.

It is a preferred feature of all aspects and embodiments of the invention for the dosage formulations to be bioadhesive or mucoadhesive. As used herein, the term "mucoadhesive" means a formulation which adheres to a mucosal surface. As used herein, the term "bioadhesive" means a formulation which adheres to the surface of biological tissue.

That is to say that the formulations coat the surface and should remain even when this surface is subject to a flow of air or liquid and/or rubbing. It is particularly preferable that the formulations should be stable to rinsing with water. For example, a formulation may be applied to a body surface and be exposed to a flow of five hundred times its own volume of water per minute for 5 minutes. After this treatment, the formulation can be considered bioadhesive if less than 50% of the formulation or bioactive agent has been lost. Preferably this level of loss will be matched when water equalling 1000 times and more preferably 10,000 times the volume of the composition is flowed past per minute for five, or preferably 10, minutes.

It is especially preferred for films and patches according to the invention to be mucoadhesive and/or bioadhesive.

In a preferred embodiment applicable to all aspects of the invention, the solid pharmaceutical dosage formulations have a laminated core comprising multiple layers, wherein each layer comprises a drug suspended in a matrix comprising:

(a) an excipient which absorbs electromagnetic radiation at a wavelength of 200 nm to 11 µm, preferably 315 nm to 1.4 µm, more preferably 380 nm to 800 nm, preferably 400 nm to 610 nm;

or
(a) an excipient; and
(b) an absorbent material which absorbs electromagnetic radiation at a wavelength of 200 nm to 11 µm, preferably 315 nm to 1.4 µm, more preferably 380 nm to 800 nm, preferably 400 nm to 610 nm.

In a preferred embodiment applicable to all aspects of the invention, the solid pharmaceutical dosage formulations have a laminated core comprising multiple layers, wherein each layer comprises a drug, an excipient, and optionally an absorbent material.

The drug, excipient and absorbent material may be as hereinbefore discussed and defined.

Preferably the laminated core comprises at least 2, more preferably at least 3 layers. In one embodiment, applicable to all aspects of the invention the laminated core comprises not more than 500 layers, more preferably not more than 300 layers. Preferably the laminated core comprises from 3 to 200 layers, more preferably from 10 to 100 layers, for example 20 to 80 layers, such as about 50 layers.

Preferably, the thickness of each layer in the laminated core may be within the range from 0.01 mm to 10 mm, more preferably 0.01 mm to 0.5 mm.

Without wishing to be bound by theory it is believed that during powder bed fusion 3DP according to the processes of the invention the excipient, and absorbent material if present, form a melt or solid-solution in which the drug is molecularly dispersed/dissolved. This melt is referred to herein as a "matrix".

Throughout this application the term "matrix" applies to the mixture of excipients such as polymer(s) and other excipients such as fillers, diluents, lubricants, plasticizer, if present, and may also be applied to the cooled and solidified mixture as well as the molten mixture. The term "matrix" does not require a chemical reaction or change in the chemical structure of the excipient, such as might be found upon curing, for example. Preferably the matrix is uncured.

Uses

In another aspect the invention provides the use of powder bed fusion selective laser 3-dimensional printing for the production of a solid pharmaceutical dosage formulation having a laminated core comprising multiple layers, each layer comprising:
(a) a drug, and
(b) an excipient
wherein at least one of said drug and said excipient absorbs electromagnetic radiation at a wavelength emitted by the laser;
or
(a) a drug;
(b) an excipient; and
(c) an absorbent material which absorbs electromagnetic radiation at a wavelength emitted by the laser.

In a further aspect the invention provides the use of an absorbent material in powder bed fusion selective laser 3-dimensional printing for the preparation of a solid pharmaceutical dosage formulation, said use comprising addition of said absorbent material to a mixture comprising a drug and an excipient prior to undergoing printing, wherein said absorbent material absorbs electromagnetic radiation at a wavelength emitted by the laser.

In a yet further aspect the invention provides the use of a mixture comprising:
(a) a drug; and
(b) an excipient
wherein at least one of said drug and said excipient absorbs electromagnetic radiation at a wavelength emitted by the laser;
or
(a) a drug;
(b) an excipient; and
(c) an absorbent material which absorbs electromagnetic radiation at a wavelength emitted by the laser;
in powder bed fusion selective laser 3-dimensional printing, to provide a solid pharmaceutical dosage formulation.

Preferably in the uses of the invention the said drug, said excipient, said absorbent material and/or said 3-dimensional printing are as defined and discussed previously.

It is preferred in the uses of the invention if the said solid pharmaceutical dosage formulation is a solid pharmaceutical dosage formulation according to the invention.

Kit

In a further aspect the invention provides a kit for producing a solid pharmaceutical dosage formulation, comprising a powder bed fusion selective laser 3-dimensional printer; and further comprising:
(a) a drug; and
(b) an excipient
wherein at least one of said drug and said excipient absorbs electromagnetic radiation at a wavelength emitted by the laser;
or
(a) a drug;
(b) an excipient; and
(c) an absorbent material which absorbs electromagnetic radiation at a wavelength emitted by the laser.

Preferably in the kit of the invention the said drug, said excipient, said absorbent material and/or said 3-dimensional printing are as defined previously with respect to the process of the invention.

It is preferred in the kit of the invention if the said solid pharmaceutical dosage formulation is a solid pharmaceutical dosage formulation according to the invention.

BRIEF DESCRIPTION OF FIGURES

FIG. 1: Schematic of Powder Bed Fusion Selective Laser 3DP Methods
FIG. 2: Schematic of SLS 3DP
FIG. 3: typical 3DP geometries
FIG. 4: 3DP geometries from examples
FIG. 5: 3DP geometries from examples
FIG. 6: Drug release results for example formulations
FIG. 7: SEM Micrographs of Kollicoat IR+Mannitol+Paracetamol+Colourant as absorbant material (71%/20%/5%/3%) at different laser scan speeds
FIG. 8: Cardurin colourants used as absorbent material under the previously detailed testing conditions show high absorbance (>0.2) at 445 nm. PVA polymer shows absorbance lower than 0.01 (PVA cannot be sintered). Mixtures of PVA and different concentrations of Candurin Gold (colourant) show absorbance values higher than 0.01 and the mixtures can be sintered to obtain oral dosage forms.
FIG. 9: Absorbance values of some polymers and the drug paracetamol under the same conditions. Shellac has an absorbance higher than 0.01 at 445 nm and it can be sintered without using any other absorbent material
FIG. 10: Kollidon VA-64 0.1 mm diameter pellets
FIG. 11: Polypill containing paracetamol and salicylic acid in two different layers
FIG. 12: 80% paracetamol loaded tablet according to example 8

FIG. 13: Tablets made of PEO 100 KDa containing the drug 4-ASA printed with three different laser scanning speeds. From left to right: 200, 300, 400 mm/s

EXAMPLES

A desktop SLS printer from Sintratec (Sintratec Kit, Switzerland) with a blue diode laser of 2.3 W was used.

TABLE 3

Comparison of Sintratec printer with other SLS printers

| Printer | Sintratec | Other printers |
|---|---|---|
| Laser type | Blue diode Laser | CO2 laser, infrared light |
| Laser power | 2.3 W | 2 to 140 W |
| Wavelength | 445 nm | 9.4 to 10.6 μm |
| Surface temperature | 80 to 180° C. | — |
| Chamber temperature | 60 to 150° C. | — |
| Scan speed | 30 to 200 mm/s. | 1270-12700 mm/s |
| Beam spot size | 0.2 mm | — |

In the examples the sintering process is promoted by the use of colourants as absorbent materials. These absorb the laser energy more efficiently. The use of a colourant is not a requirement if the drug or excipient absorbs light at the right wavelength. The inventors have evaluated different colourants used in the pharmaceutical industry e.g. Iron oxide or Carmine, Cardurin Orange (Merck, UK), which showed very good performance.

A polymer was used as excipient, having a relatively low transition glass temperature (Tg) and a colourant was used as absorbent material. 3% of colourant was used with, for example, polymers including Eudragit L-100-55, Kollidon VA-64, Kollicoat IR and Polyethylene oxide.

Drug release tests in biorelevant media have been used to demonstrate drug release profiles which can be varied dependent on the polymer composition of the tablets or films and associated methodologies. For example it is possible to achieve immediate release of the drug (or drugs) using formulations incorporating Kollicoat IR and to achieve modified release for cellulose derivatives such as hydroxypropyl cellulose, hydroxypropyl methyl cellulose and acrylic polymers such as Eudragit L100.

For example, it has proved possible to achieve very rapid disintegration by creation of films prepared with polyethyleneoxide.

SLS 3DP has also been used to generate formulations which can adhere to surfaces (such as the inside of the mouth) i.e. are bioadhesive or mucoadhesive, and allow gradual drug release in that environment.

Examples of drug release profiles from several formulations are shown in FIG. 3.

Results to date highlight for the first time the potential of SLS 3D printing to fabricate solid dosage forms such as oral tablets, buccal films and topic masks with defined drug release characteristics and in principle will allow the use of SLS 3D printing of appropriate excipients for manufacture of medicines with doses which are tailored to the patient. This productive system could be also adapted to the industrial scale for production of medicines avoiding other manufacturing methods as tableting or processing drawbacks as large batch productions.

Example 1: Preparation of Drug-Loaded Printed Pharmaceutical Dosage Formulations by SLS 3DP A mixture of excipient, absorbent material and 5% paracetamol was prepared using a mortar and pestle. Paracetamol was used as a model drug. A polymer excipient having a relatively low glass transition temperature (Tg) was used in combination with a colourant (3-10%) as the absorbent material. Some of the polymers successfully tested include Eudragit L-100-55, Kollicoat IR and Polyethylene oxide.

TABLE 4

Formulations printed by SLS

| | % | | PRINTING PARAMETERS | | |
|---|---|---|---|---|---|
| Excipient | Absorbent material (Gold Colourant) | % Drug (Paracetamol) | Chamber Temp in ° C. | Surface Temp in ° C. | Laser scan speed in mm/sec |
| PVA 87-89% HYDROLISED (MW 13-23 Kda) | 3 | 5 | 170 | 150 | 110 |
| PVA 87-90% HYDR. (MW 30-70 Kda) | 3 | 5 | 170 | 150 | 70 |
| PVA NIPPON GOHSEI | 3 | 5 | 130 | 95 | 60 |
| KOLLICOAT IR (PEG 25% + PVA 75%) | 3 | 5 | 120 | 90 | 90 |
| KOLLICOAT PROTECT (KOLLICOAT IR + PVA) | 3 | 5 | 120 | 90 | 90 |
| PVA 87-89% HYDROLISED (MW 13-23 Kda) + MANNITOL (50/50) | 3 | 5 | 160 | 140 | 110 |
| PVA 87-89% HYDROLISED (MW 13-23 Kda) + MANNITOL (35/65) | 3 | 5 | 150 | 130 | 110 |
| PVA NIPPON + PEO 7M (80/20) | 4 | 5 | 135 | 120 | 64 |
| KOLLICOAT IR + MANNITOL (80 + 20) | 3 | 5 | 120 | 94 | 100 |

TABLE 4-continued

Formulations printed by SLS

| Excipient | % Absorbent material (Gold Colourant) | % Drug (Paracetamol) | Chamber Temp in °C. | Surface Temp in °C. | Laser scan speed in mm/sec |
|---|---|---|---|---|---|
| KOLLICOAT IR + MANNITOL (60 + 40) | 3 | 5 | 130 | 120 | 150 |
| KOLLICOAT IR + MANNITOL SIGMA (80/20) | 3 | 5 | 130 | 100 | 70 |
| KOLLICOAT IR + MANNITOL SIGMA (60/40) | 3 | 5 | 130 | 100 | 200 |
| EUDRAGIT L100-55 | 3 | 5 | 120 | 80 | 80 |
| EUDRAGIT RS PO | 3 | 5 | 65 | 54 | 70 |
| EUDRAGIT RL PO | 3 | 5 | 65 | 54 | 70 |
| EUDRAGIT FS100 | 3 | 5 | 65 | 52 | 100 |
| EUDRAGIT S100 | 10 | 5 | 130 | 100 | 55 |
| EUDRAGIT L100 | 5 | 5 | 130 | 100 | 60 |
| EUDRAGIT L100-55 + PEO 600 Kda (70/30) | 3 | 5 | 85 | 60 | 45 |
| EUDRAGIT L100-55 + PEO 7M (90/10) | 5 | 5 | 90 | 60 | 40 |
| EUDRAGIT L100-55 + PEO 7M (95/5) | 5 | 5 | 90 | 60 | 40 |
| EUDRAGIT L100-55 + PEO 7M (90/10) | 5 | 5 | 140 | 115 | 60 |
| EUDRAGIT L100-55 + PEO 7M (90/10) | 5 | 5 | 140 | 115 | 60-75 |
| EUDRAGIT L100-55 + PEO 7M (80/20) | 5 | 5 | 135 | 115 | 70 |
| EUDRAGIT L100-55 + PEO 7M (90/10) DOUBLE LAYER | 5 | 5 | 140 | 115 | 60 |
| HPMC ASHLAND BENECEL K100LV PH PRM | 3 | 5 | 140 | 160 | 100 |
| HPMC ASHLAND BENECEL K4M PHARM CR | 3 | 5 | 140 | 166 | 100 |
| MC BENECEL A15LV PH PRM | 3 | 5 | 140 | 166 | 101 |
| HEC HERCULES NATROSOL Pharm 250M PHARM | 3 | 5 | 100 | 125 | 80 |
| HPC KLUCEL ASHLAND LF PHARM | 6 | 5 | 100 | 130 | 75 |
| HPC KLUCEL ASHLAND EF PHARM | 3 | 5 | 100 | 130 | 35 |
| HPC KLUCEL ASHLAND MF PHARM | 3 | 5 | 100 | 135 | 38 |
| HPC KLUCEL ASHLAND GF PHARM | 6 | 5 | 100 | 130 | 75 |
| CELLULOSE ACETATE ALDRICH 39.8% ACETYL CONTENT MW 30000 | 3 | 5 | 120 | 100 | 100 |
| ETHYLCELLULOSE DOW | 3 | 5 | 130 | 105 | 85 |
| ETHYLCELLULOSE ALDRICH 46 Cp | 3 | 5 | 130 | 109 | 50 |
| ETHYLCELLULOSE (AQUALON EC-N7) | 3 | 5 | 130 | 100 | 93 |
| ETHYLCELLULOSE ACROSS CP 10 | 3 | 5 | 130 | 100 | 70 |
| ETHYLCELLULOSE ACROSS 10 cps + PEO 7M (90/10) | 3 | 5 | 125 | 105 | 90 |
| AQOAT AS-LG SHIN ETSU | 3 | 5 | 130 | 100 | 90 |

TABLE 4-continued

Formulations printed by SLS

| Excipient | % Absorbent material (Gold Colourant) | % Drug (Paracetamol) | Chamber Temp in °C. | Surface Temp in °C. | Laser scan speed in mm/sec |
|---|---|---|---|---|---|
| AQOAT AS-MG SHIN ETSU | 3 | 5 | 130 | 100 | 90 |
| AQOAT AS-HG SHIN ETSU | 3 | 5 | 130 | 100 | 90 |
| AQOAT AS-MG + PEO 7M (90/10) | 3 | 5 | 125 | 105 | 120 |
| POLYOX 100 Kda | 3 | 5 | 55 | 35 | 100 |
| POLYOX N-12 K | 3 | 5 | 55 | 33 | 35-70 |
| PEO 8M SIGMA | 3 | 5 | 60 | 40 | 35 |
| PEO 300 KDa + SHELLAC SSB 55 (50/50) | 1.5 | 5 | 70 | 55 | 30 |
| PEO 300 KDa + KOLLIPHOR P188 (50/50) | 3 | 5 | 50 | 36 | 150 |
| PEO 300 KDa + EUDRAGIT RS PO (50/50) | 3 | 5 | 65 | 50 | 35-70 |
| SHELLAC WAX-FREE SIGMA | None | 5 | 60 | 50 | 125 |
| SHELLAC SSB 55 | None | 5 | 60 | 50 | 50 |
| SHELLAC SSB 55 + PVA NIPPON (60/40) | None | 5 | 55 | 40 | 40 |
| SHELLAC SSB 55 + PVA NIPPON (50/50) | None | 5 | 62 | 54 | 18 |
| SHELLAC SSB 55 + KOLLICOAT IR (50/50) | 1.5 | 5 | 60 | 40 | 20 |
| SHELLAC SSB 55 + XANTHAN GUM (50/50) | None | 5 | 70 | 50 | 29 |
| SHELLAC SSB 55 + EUDRAGIT RS PO (50/50) | 1 | 5 | 70 | 60 | 60 |
| SHELLAC SSB 55 + MANNITOL (70/30) | None | 5 | 75 | 60 | 19 |
| PVP 40000 MW SIGMA | 3 | 5 | 150 | 120 | 50 |
| PVP 10000 MW SIGMA | 3 | 5 | 150 | 120 | 130 |
| PVP360000 MW SIGMA | 3 | 5 | 160 | 150 | 70 |
| PVP SIGMA 360 KDa + PEO 7M (90/10) | 3 | 5 | | | |

A standard desktop SLS 3D printer Sintratec (Sintratec Kit, Switzerland) was used to fabricate the pharmaceutical dosage forms from the mixture. This SLS printer uses a laser of 445 nm wavelength (2.3 W potency) to sinter the powder.

The mixture must include a material that absorbs at the wavelength of the laser in order for the sintering process to take place without degradation of the drug. This can be achieved by having a drug and/or excipient which absorbs in the appropriate region, and/or using an absorbent material.

These examples use a colourant as absorbent material. We have evaluated different colourants used in the pharmaceutical industry e.g. Iron oxide or Carmine, and Cardurin Orange (Merck, UK).

The templates used to print the formulations were designed with AutoCAD 2014® (Autodesk Inc., USA) and exported as a stereolithography file (.stl) into the 3D printer software. The printer settings (temperature of the chamber and laser speed) were selected depending on the characteristics of the polymer excipient.

The basic selected 3D geometries were a cylinder shape tablet (10 mm length×5 mm diameter) and a square patch/film (20 mm length). It was possible to manufacture different types of drug-loaded dosage forms, including tablets of different shapes, films that could be used for buccal delivery, and topical delivery patches.

Example 2: Determination of Drug Loading

Tablets weighing approx. 300 mg, prepared as in example 1, were placed in a volumetric flask with deionized water (1 L) under magnetic stirring until complete dissolution.

Samples of the solutions were then filtered through 0.45 µm filters (Millipore Ltd, Ireland) and the concentration of drug determined with high performance liquid chromatograph (HPLC). We used a Hewlett Packard 1050 Series HPLC system, Agilent Technologies, UK. The validated high performance liquid chromatographic assay entailed injecting 20 µL samples for analysis using a mobile phase, consisting of gradient system of (A) water adjusted to pH 2 with orthophosphoric acid and (B) acetonitrile, through a Luna 5 µm C18 column, 150×4.6 mm (Phenomenex, UK)

maintained at 40° C. The mobile phase was pumped at a flow rate of 1 mL/min under the following gradient program: 0-15 min, 5-20% B; 15-16 min, 20-5% B.

HPLC results showed there was no drug degradation during the printing process.

Example 3: Dissolution Test of the Tablet

The drug release performance from the tablets produced according to example 1 was evaluated using a USP-II apparatus (Model PTWS, Pharmatest, Germany). The tablets were placed for 2 h into 750 mL of 0.1 M HCl and subsequently into 1000 mL of 0.05M phosphate buffer (pH 6.8). The paddle speed of the USP-II was fixed at 50 rpm and the tests were conducted at 37+/−0.5° C. The percentage of drug released from the tablets was determined using an in-line UV spectrophotometer (Cecil 2020, Cecil Instruments Ltd., UK) at 244 nm. Data were processed using Icalis software (Icalis Data Systems Ltd, UK).

Drug release profiles from the different formulations show a wide variety of dissolution profiles depending on the composition of the formulations (see FIG. 6). Burst release is shown for some formulations while controlled-release is shown for another.

The selection of the printing parameter, e.g. laser speed or temperature, affects the drug release from the 3D printed formulations. FIG. 7 shows SEM micrographs of Kollicoat IR+Mannitol+Paracetamol+gold colourant as absorbant material (71%/20%/5%/3%) at different laser scan speeds. Formulations are shown in table 5 below.

TABLE 5

Formulations of tablets shown in FIG. 7

| Excipients | % Absorbant Material (Gold Colourant) | Paracetamol | PRINTING PARAMETERS | | | |
|---|---|---|---|---|---|---|
| | | | CHAMBER TEMP (° C.) | SURFACE TEMP (° C.) | LASER SPEED (mm/sec) | Dissolution time (min) |
| KOLLICOAT IR + MANNITOL + PARACETAMOL (71/20/5) | 3 | 5 | 120 | 94 | 200 | 0.5 |
| KOLLICOAT IR + MANNITOL + PARACETAMOL (71/20/5) | 3 | 5 | 120 | 94 | 600 | 5 |

Example 4: Disintegration Test of the Films

The disintegration test performance of the films made according to example 1 was evaluated using a Petri dish placed on a moving surface (Plate shaker IKA, UK) at 50 rpm. The films were placed in 5 mL of deionised water and the time that the film took to undergo disintegration was recorded.

The disintegration time was dependent on the excipient and on the printing temperatures, ranging from 30 s (Polyethylene oxide) to more than 1 h (Eudragit L100-55).

Example 5: Measurement of Absorbance

Absorbance of the drug and/or excipient and/or absorbent material which absorbs electromagnetic radiation at a wavelength emitted by the laser may be measured by spectroscopy. For example, UV-Vis-NIR spectrophotometers are available from manufacturers including Shimadzo (e.g. UV-2600, UV-2700). Absorbance, such as at wavelengths between 200-1400 nm, can be measured by UV-Vis-NIR spectroscopy at room temperature (approximately 25° C.) using a reflecting chamber. "Diffuse Reflectance Accessory (DRA)".

Here 0.15 g of material to be evaluated (e.g. polymers or mixture of polymer and drug) is blended with 0.5 g of barium sulphate that is compressed and introduced in the spectrophotometer. FIGS. 8 and 9 show measurements under these conditions In FIG. 8 Cardurin colorants used as absorbent material under the previously detailed testing conditions show high absorbance (>0.2) at 445 nm. PVA polymer shows absorbance lower than 0.01 (PVA cannot be sintered). Mixtures of PVA and different concentrations of Candurin Gold (colorant) show absorbance values higher than 0.01 and the mixtures can be sintered to obtain oral dosage forms.

FIG. 9 shows absorbance values of some polymers and the drug paracetamol. Shellac has an absorbance higher than 0.01 at 445 nm and it can be sintered without using any other absorbent material.

Example 6: Preparation of Drug-Loaded Pellets Printed by SLS

Pellets of 1 mm diameter were prepared using 92% Kollidon VA-64, 5% Paracetamol, 3% Candurin Gold Sheen (FIG. 10). Laser scanning speed was 100 mm/s, chamber temperature 80° C. and surface temperature 100° C.

Example 7: Preparation of Drug-Loaded Polypills Printed by SLS

Polypills made with layer of different composition were prepared containing different drugs (FIG. 11)

The composition of the layers of the polypill is:

Top layer (red): 92% Kollidon VA-64, 5% Salicylic Acid, 3% Candurin red sparkle—Laser scanning speed was 100 mm/s, chamber temperature 80° C. and surface temperature 100° C. Bottom layer (yellow): 92% Kollidon VA-64, 5% Paracetamol, 3% Candurin gold sheen—Laser scanning speed was 100 mm/s, chamber temperature 80° C. and surface temperature 100° C.

Example 8: Preparation of Tablets Incorporating High Drug Loading Printed by SLS Tablets incorporating 80% paracetamol were prepared using 17% Eudragit L100-55 and 3% Candurin gold sheen (FIG. 12). Laser scanning speed was 90 mm/s, chamber temperature 90° C. and surface temperature 110° C.

Example 9: Preparation of Tablet Incorporating 4-ASA Printed by SLS Highly (FIG. 12)

Tablets prepared with the drug 4-ASA were successfully printed with three different laser scanning speeds (200, 300, 400 mm/s) (FIG. 13). Composition of the tablet: 92% PEO 100 KDa, 5% 4-ASA, 3% Candurin Gold sheen. Chamber temperature was 35° C. and surface temperature 50° C.

HPLC drug loading studies have been performed. No degradation of the 4-ASA drug was found to have taken place during the printing process using SLS. This is a significant advantage compared to FDM printing that was found to degrade the drug 4-ASA while printing. (Goyanes et al. 3D printing of modified-release aminosalicylate (4-ASA and 5-ASA) tablets. Eur. J. Pharm. Biopharm. 89, 157-162).

Conclusions

It was possible to produce with SLS 3DP a great variety of formulations (tablets, films or patches) pre-loaded with drugs and suitable for use as pharmaceutical dosage formulations.

The formulations show a wide variety of dissolution rates (for tablets) and disintegration speeds (for films) that depends on the composition of the formulations.

The invention claimed is:

1. A process comprising: powder bed fusion selective laser 3-diminsional printing of a powder mixture comprising: (a) a drug; and (b) an excipient; wherein at least one of said drug and said excipient absorbs electromagnetic radiation at a wavelength emitted by the laser; or (a) a drug; (ab) an excipient; and (c) an absorbent material with absorbs electromagnetic radiation at a wavelength emitted by the laser, the absorbent material selected from the group consisting of iron oxide, titanium oxide, silicates, carmine, candurin, phtalacyanine, diazos, or mixtures thereof; and producing an oral formulation to the exclusion of a surgically inserted implant.

2. The process as claimed in claim 1, wherein said powder bed fusion selective laser 3-dimensional printing comprises selective laser sintering 3-dimensional printing or selective laser melting 3-dimensional printing, or a mixture thereof.

3. The process as claimed in claim 1 wherein said excipient absorbs electromagnetic radiation at a wavelength emitted by the laser.

4. The process as claimed in claim 1 wherein said electromagnetic radiation is electromagnetic radiation within the infrared, visible or ultraviolet regions of the electromagnetic spectrum.

5. The process as claimed in claim 1 wherein the laser power is at least 1.5 W.

6. The process as claimed in claim 1 wherein said mixture is a heterogeneous mixture.

7. The process as claimed in claim 1 wherein the laser emits electromagnetic radiation having a wavelength in the range of from 200 nm to 11 μm without degradation of the drug.

8. The process as claimed in claim 1 wherein said printing is performed using a scan speed in the range of from 20 mm/s to 300 mm/s;

and/or wherein said printing is performed using a surface temperature in the range of 40-180° C.

9. The process as claimed in claim 1 wherein said mixture comprises from 0.01 wt. % to 85 wt. % of the said drug by total weight of the mixture.

10. The process as claimed in claim 1 wherein said mixture comprises two or more excipients;

and/or wherein said mixture comprises from 15 wt. % to 99.5 wt. % of the said excipients by total weight of the mixture.

11. The process as claimed in claim 1 wherein the said excipient comprises or consists of a polymer;

optionally wherein said polymer comprises at least one enteric polymer; or wherein said polymer comprises at least one pH-independently soluble polymer;

and/or wherein said polymer has a glass transition temperature in the range of from −100° C. to 250° C.

12. The process as claimed in claim 11 wherein said polymer is selected from the group consisting of methyl acrylate-methacrylic acid copolymers, ethyl acrylate-methacrylic acid copolymers, cellulose acetate succinate, hydroxy propyl methyl cellulose phthalate, hydroxypropylmethyl cellulose acetate succinate, polyvinyl acetate phthalate, methyl methacrylate-methacrylic acid copolymers, shellac, cellulose acetate trimellitate, sodium alginate, zein, polyethylene oxide, ethylcellulose, hydroxypropyl cellulose, hydroxypropyl methylcellulose, polyvinylpyrrolidone, vinylpyrrolidone-vinyl acetate copolymers, gelatin, polysaccharides and mixtures thereof.

13. The process as claimed in claim 1 wherein said mixture comprises from 0.1 wt. % to 50 wt. % of the said absorbent material by total weight of the mixtures.

14. The process as claimed in claim 1 wherein said mixture comprises: (a) 1-50 wt. % of a drug selected from anti-inflammatory, steroid or antieoplastic drugs by total weight of the mixture, (b) 20-80 wt. % of an enteric polymer selected from methyl acrylate-methacrylic acid copolymers, ethyl acrylate-methacrylic acid copolymers, cellulose acetate succinate, hydroxy propyl methyl cellulose phthalate, hydroxypropylmethyl cellulose acetate succinate, polyvinyl acetate phthalate, methyl methacrylate-methacrylic acid copolymers, shellac, cellulose acetate trimellitate, sodium alginate, zein, polyethylene oxide, ethylcellulose, hydroxypropyl cellulose, hydroxypropyl methylcellulose, polyvinylpyrrolidone, vinylpyrrolidone-vinyl acetate copolymers, gelatin, polysaccharides and mixtures thereof, by total weight of the mixture; and (c) 0.1-30 wt. % of at last one absorbent material selected from the group consisting of iron oxide, titanium oxide, silicates, carmine, candurin, phthalocyanine, diazos or mixtures thereof, by total weight of the mixture.

15. A solid pharmaceutical dosage formulation produced by the process of claim 1; said solid pharmaceutical dosage formulation optionally having a laminated core comprising multiple layers, each layer comprising: (a) a drug, (b) an excipient, and (c) optionally an absorbent material selected from the group consisting of iron oxide, titianium oxide, silicates, carmine, candurin, phtalacyanine, diazos, or mixture thereof.

16. The solid pharmaceutical dosage formulation of claim 15 wherein said solid dosage formulation is bioadhesive and/or mucoadhesive.

17. A solid pharmaceutical dosage formulation, the surface of which comprises a drug and a sintered polymer and/or sintered absorbent material.

18. The solid pharmaceutical dosage formulation of claim 17 wherein said drug is suspended in a matrix comprising: (a) An excipient which absorbs electromagnetic radiation at a wavelength of 380 nm to 800 nm; or (b) an excipient; and (c) an absorbent material selected from the group consisting of iron oxide, titanium oxide, silicates, carmine, candurin, phtalocyanine, diazos, or mixtures thereof, which absorbs electromagnetic radiation at a wavelength of 380 nm to 800 nm.

19. The solid pharmaceutical dosage formulation claim 15 having a laminated core comprising multiple layers, each layer comprising: (a) a drug, (b) an excipient, and (c) optionally an absorbent material selected from the group consisting of iron oxide, titanium oxide, silicates, carmine, candurin, phtalocyanine, diazos, or mixtures thereof.

20. A process comprising: powder bed fusion selective laser 3-diminensional printing of a powder mixture comprising (a) a drug; and (b) an excipient; wherein at least one of said drug and said excipient absorbs electromagnetic radiation at a wavelength emitted by the laser; or (a) a drug; (ab) an excipient; and (c) an absorbent material which absorbs electromagnetic radiation at a wavelength emitted by the laser, the absorbent material selected from the group consisting of iron oxide, titanium oxide, silicates, carmine, candurin, phtalocyanine, diazos, or mixtures thereof; and producing an oral formulation having a controlled release of the drug.

* * * * *